(12) United States Patent
Strauss et al.

(10) Patent No.: US 9,898,579 B2
(45) Date of Patent: Feb. 20, 2018

(54) RELATIONAL DNA OPERATIONS

(71) Applicant: Microsoft Technology Licensing, LLC, Redmond, WA (US)

(72) Inventors: Karin Strauss, Seattle, WA (US); Benjamin G. Zorn, Woodinville, WA (US); Kris K. Ganjam, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 287 days.

(21) Appl. No.: 14/740,963

(22) Filed: Jun. 16, 2015

(65) Prior Publication Data

US 2016/0371434 A1    Dec. 22, 2016

(51) Int. Cl.
*G01N 33/48*     (2006.01)
*G01N 33/50*     (2006.01)
*G06F 19/28*     (2011.01)
*G06N 3/12*      (2006.01)
*C07H 21/04*    (2006.01)
*C12N 15/10*    (2006.01)
*G01N 35/00*    (2006.01)
*G01N 35/10*    (2006.01)

(52) U.S. Cl.
CPC ............ *G06F 19/28* (2013.01); *C07H 21/04* (2013.01); *C12N 15/1093* (2013.01); *G01N 35/00871* (2013.01); *G01N 35/10* (2013.01); *G06N 3/123* (2013.01)

(58) Field of Classification Search
None
See application file for complete search history.

(56) References Cited

U.S. PATENT DOCUMENTS

| 7,659,175 B2 | 2/2010 | Boland et al. |
| 2005/0053968 A1 | 3/2005 | Bharadwaj et al. |
| 2005/0069938 A1 | 3/2005 | Wang et al. |
| 2005/0177556 A1 | 8/2005 | Fang et al. |

FOREIGN PATENT DOCUMENTS

| WO | WO2013073755 | 5/2013 |
| WO | WO2013178801 | 12/2013 |

OTHER PUBLICATIONS

Second Written of the Internatonal Preliminary Examining Authority for PCT/US2016/037305, dated Apr. 26, 2017, 7 pages.
Weinberg, et al., Large-scale design of robust genetic circuits with multiple inputs and outputs for mammalian cells, published in Nature Biotechnology Jan. 2017, 12 pages.
Brijder, et al., "The DNA Query Language DNAQL", In Proceedings of the 16th International Conference on Database Theory, Mar. 18, 2013, 9 pages.
Chang, et al., "Constructing Bio-Molecular Databases on a DNA-based Computer", In Proceedings of the Computing Research Repository, Dec. 12, 2007, 35 pages.
Church, et al., "Next-Generation Digital Information Storage in DNA", Science, 2012, vol. 337 (6102), pp. 1628.
Gillis, et al., "A Formal Model for Databases in DNA", In Proceedings of 4th International Conference, Algebraic and Numeric Biology, Jul. 31, 2010, 16 pages.
Goldman, et al., "Toward Practical High-Capacity Low-Maintenance Storage of Digital Information in Synthesized DNA", Nature, 2013, vol. 494 (7435), pp. 77-80.
Kashiwamura, et al., "Hierarchical DNA Memory Based on Nested PCR", In Proceedings of 8th International Workshop on DNA-Based Computers, Jun. 10, 2002, 12 pages.
Katsanyi, "On implementing Relational Databases on DNA Strands", In Journal of Acta Cybernetica, 2003, vol. 16, pp. 259-270.
Rangwala, et al., "Massively Parallel BLAST for the Blue Gene/L", In Proceedings High Availability and Performance Computing Workshop, Oct. 2005, 6 pages.
Reif, et al., "Computationally Inspired Biotechnologies: Improved DNA Synthesis and Associative Search using Error-Correcting Codes and Vector Quantization", In Proceedings of 6th International Workshop on DNA-Based Computers: DNA Computing, Jun. 13, 2000, 22 pages.
Reif, et al., "Experimental Construction of Very Large Scale DNA Databases with Associative Search Capability", In Proceedings of 7th International Workshop on DNA-Based Computers, Oct. 13, 2001, 10 pages.
Schuster, "DNA Databases", Biosystems, 2005, vol. 81 (3), pp. 234-246.
Tsuboi, et al., "DNA Computing Approach to Semantic Model", International Journal of Computer Science & Applications, 2014, vol. 2 (2), pp. 118-130.
Yamamoto, et al., "Development of DNA Relational Database and Data Manipulation Experiments", In Proceedings of the 12th international conference on DNA Computing, Jun. 5, 2006, pp. 418-427.
Cardelli, Luca, "Strand Algebras for DNA Computing", In Journal—Natural Computing, Kluwer Academic Publishers, vol. 10, Issue 1, Nov. 27, 2010, pp. 407-428.

(Continued)

*Primary Examiner* — Russell S Negin
(74) *Attorney, Agent, or Firm* — Schwegman Lundberg & Woessner, P.A.

(57) ABSTRACT

A database implemented by storing information encoded in DNA molecules provides high information density but the information is more difficult to access than in conventional electronic storage media. A relational database is a way of organizing information by using multiple related tables. Relational algebra operations are performed on relational databases to locate and manipulate information. This disclosure provides techniques for implementing relational algebra operations on a relational database that uses DNA molecules to store information. The techniques of this disclosure relate to the structure of DNA molecules used to store the information and to correlations between relational algebra operations and manipulations of DNA molecules.

14 Claims, 11 Drawing Sheets

(56) References Cited

OTHER PUBLICATIONS

Chang, et al., "DNA Algorithms of Implementing Biomolecular Databases on a Biological Computer", In the Proceedings of IEEE Transactions on Nanobioscience, vol. 14, Issue 1, Jan. 1, 2015, pp. 103-110, 8 pages.

"International Search Report and Written Opinion Issued in PCT Application No. PCT/US2016/037305", dated Sep. 19, 2016, 13 Pages.

Baum, "Building an Associative Memory Vastly Larger than the Brain" Science, 1995, vol. 268 (5210), pp. 583-585.

RELATIONAL DNA OPERATIONS

BACKGROUND

Polymers of deoxyribose nucleic acid (DNA) are capable of storing information at high density. A gram of DNA contains about $10^{21}$ DNA bases which can encode about $10^8$ terabytes of data. The information density of DNA is about $10^8$ times more compact than other types of storage media. Less than 100 grams of DNA could store all the human-made data in the world. Thus, DNA is appealing as an information storage technology because of its high information density. Information encoded by DNA is first converted to a format that can be processed by digital computing technology before presentation in a human-readable form. Converting a whole DNA digital data storage into electronic format whenever information is retrieved would be inefficient and negate the advantage of storing the information as DNA. Techniques to identify particular DNA molecules containing information of interest reduce the amount of information that is converted into electronic format and can improve the usability of DNA as an information storage medium.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

This disclosure provides techniques to manipulate DNA molecules that are used to store information in a DNA digital data storage organized as a relational database. The techniques correspond to relational algebra operations that are performed on conventional relational databases storing information electronically. DNA molecules following manipulation according to these techniques may be sequenced to convert the information encoded by the DNA into electronic form for further processing and use.

A digital computer that interfaces with a database management system (DBMS) can receive one or more relational algebra operation specifying one or more tables in the DNA digital data storage. The table may be designated by a table-ID sequence encoded in DNA molecules that contain information from the table. The digital computer can also identify DNA manipulations which correspond to the relational algebra operation. The DNA manipulations may include hybridizing a complementary DNA sequence to at least a portion of the table-ID sequence. Instructions to perform the DNA manipulations are sent to the DNA digital data storage for implementation by the DBMS on the DNA in the DNA digital data storage. After the DNA digital data storage implements the instructions, the digital computer may receive a DNA sequence from the DNA digital data storage.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
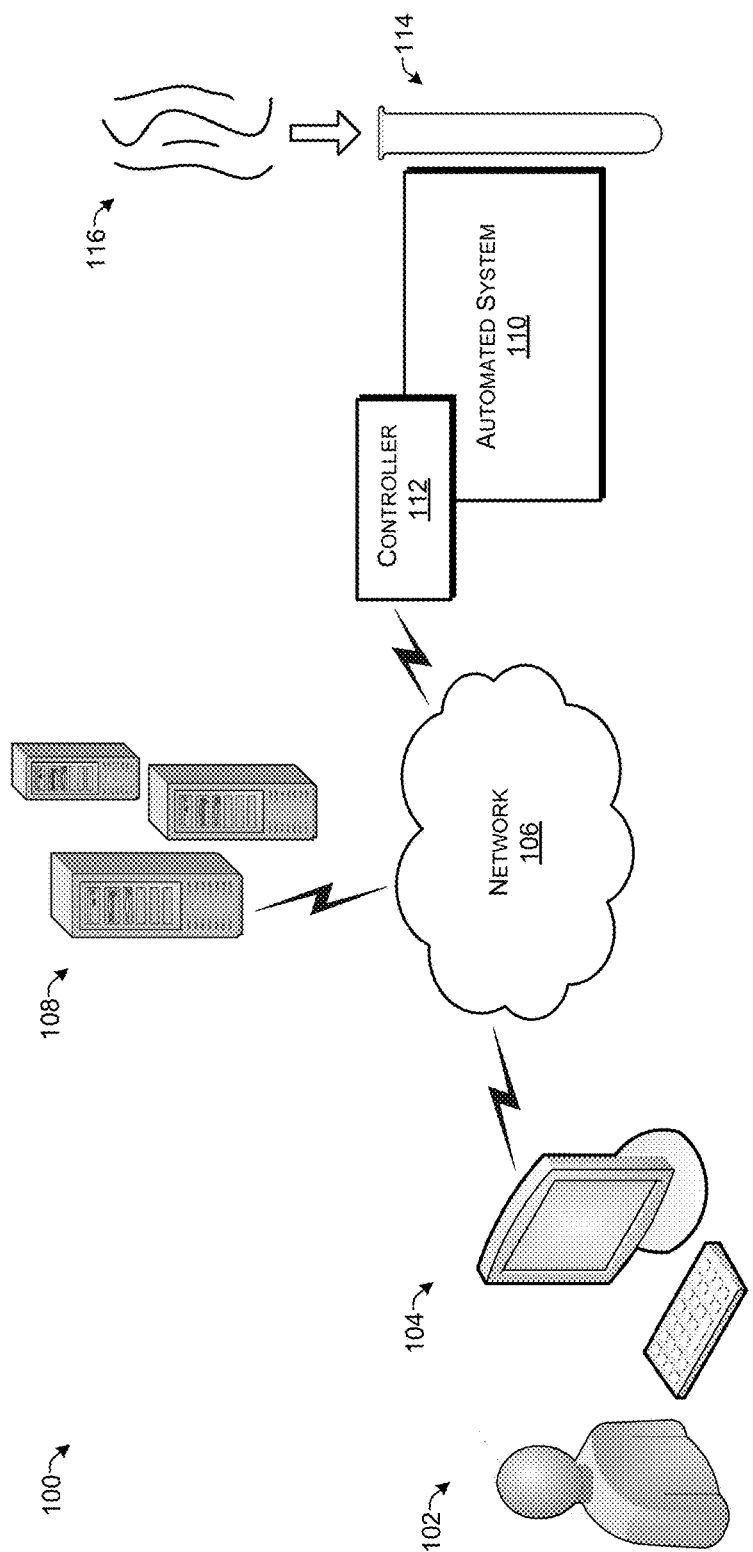
FIG. 1 shows an illustrative architecture for interfacing between digital computers and a DNA digital data storage.

A DNA digital data storage that is organized as a relational database takes advantage of the high information density provided by DNA and uses the conceptual organizational structure of a relational database. Relational algebra operations that are used to interact with relational databases implemented in conventional electronic storage media may also be used with DNA digital data storage. However, implementing relational database operations on molecules of DNA requires molecular biology techniques that are not needed when working with electronic databases. This disclosure provides techniques for implementing relational algebra operations on a relational database that uses DNA molecules to store information. The techniques of this disclosure relate to the structure of DNA molecules used to store the information and to correlations between relational algebra operations and manipulations of DNA molecules.

A relational database is a database that organizes stored information according to a metaphor of tables having rows and columns. A table is referred to as a relation in the sense that it is a collection of entities or objects of the same type (e.g., employees of a business) each represented by a row in the table. Each row, also called a record or tuple, of a table is represented by a unique key which can be a descriptive name or any arbitrary sequence of number and/or letters that uniquely identifies the row. Fields, also referred to as attributes, are stored in a table and shared across multiple columns. The intersection of a row (e.g., employee named Smith) with a column (e.g., phone number) provides the value of a field for an entry (e.g., 867-5309, the phone number for Smith). Data in a table can be related according to common keys or concepts, and the ability to retrieve related data from a set of tables is the basis for the term relational database. Relationships between tables within a relational database are useful for accessing and manipulation information stored in a database. Relational algebra provides a theoretical foundation for management of relational databases. Relational algebra includes many fundamental or "primitive" operations from which more complex operations can be derived.

Although many relational databases are currently implemented as electronic records directly accessible by digital computers, there is no requirement that a relational database be implemented electronically. DNA, which encodes biological information that instructs cellular machinery how to build proteins, can also be used as a data storage technology for human-generated information. Artificial synthesis of DNA allows for creation of DNA molecules with arbitrary series of the bases cytosine (C), guanine (G), adenine (A), thymine (T), and non-standard bases such as synthetic bases. The order in which individual monomers of these four bases are assembled together into a polymer can represent information in an analogous manner as 0 and 1 in digital computers. Thus, multiple DNA molecules can be synthesized with particular orders of the four DNA bases and encode large amounts of information.

DNA molecules are generally most accessible for manipulation by bio-technological techniques when the DNA is stored in a liquid solution. Thus, a DNA digital data storage can be implemented as a chamber filled with liquid, in many implementations water, and thousands, millions, or more individual DNA molecules. In many implementations the information encoded by the DNA molecules is obtained through sequencing. Sequencing uses a machine, a sequencer, to read the order of the DNA bases in a given DNA molecule. The sequencer provides output in electronic format that can be manipulated by conventional digital computers. Human users will typically interact with the information contained in a DNA digital data storage through use of a digital computer. Adding new information to the DNA digital data storage, making a query to the DNA digital data storage, changing information to the DNA digital data storage and other types of interactions can be initiated at the user interface of the digital computer, implemented partially or completely by manipulating the actual DNA molecules in solution, and lead to a result generated by sequencing certain DNA molecules.

Thus, relational algebra operations performed on relational databases are implemented on DNA digital data storages by performing specific DNA manipulations that manipulate the DNA molecules in order to access information in accordance with the corresponding relational algebra operations. For some relational algebra operations, manipulation of the DNA may not be sufficient and will be supplemented by additional computation once the information encoded by the DNA sequences is converted to electronic form. Therefore, the manipulations performed on the DNA may serve to identify and isolate a subset of DNA molecules from the large number of molecules stored in a DNA digital data storage. Once isolated, sequencing of this reduced number of DNA molecules and subsequent processing of information in electronic form becomes more efficient than dealing with all of the DNA molecules in a given DNA digital data storage.

Relational algebra operations include selection, projection, intersection, rename, natural join, and Cartesian product. Each of these is discussed below. As algebraic or mathematical operations applied to information, the relational algebra operations are the same whether implemented on electronic information or information stored in another format such as DNA. Programming languages such as Structured Query Language (SQL) manage relational databases by implementing relational algebra operations on electronically stored information. It is also possible to use SQL for describing operations implemented on the DNA domain.

Selection is an operation with only one input that is written as $\sigma_\phi(R)$ where $\phi$ is a propositional formula that consists of simple formulas that cannot be reduced further and the logical operators $\wedge$ (and), $\vee$ (or) and $\neg$ (negation). This selection selects all those rows in R for which $\phi$ holds. To obtain a listing of all friends or business associates in an address book, the selection might be written as $\sigma_{isFriend=true} \vee {}_{isBusinessContact=true}$(addressBook). The result would be a relation containing every attribute of every unique record where isFriend is true or where isBusinessContact is true.

Projection is an operation with only one input that is written as $\Pi a_1, \ldots, a_a(R)$ where $a_1, \ldots, a_n$ is a set of attribute names. The result of such projection is defined as the set that is obtained when all rows in R are restricted to the set $\{a_1, \ldots, a_n\}$. This specifies the specific subset of columns (attributes of each row) to be retrieved. To obtain the names and phone numbers from an address book, the projection might be written $\Pi_{contactName, contactPhoneNumber}$(addressBook). The result of that projection would be a table which contains only the contactName and contactPhoneNumber attributes for each unique entry in the addressBook.

Intersection is an operation that produces a set of rows that two or more relations (i.e., tables) share in common. The intersection operation between relations R and S is written as R∩S and returns the rows that are present in both R and S. Intersection is an associative operation that can be applied to more than two tables. For example, to find records that exist in both a table of friends and a table of business contacts $\cap_{isFriend/isBusinessContact}$(addressBook) might be used to return those rows that are present in both tables.

Rename is an operation with only one input that is written as $\rho_{a/b}(R)$ where the result is identical to R except that the b attribute in all rows is renamed to a attribute. This is simply used to rename the attribute of a table or rename the table itself. To rename the 'isFriend' attribute to 'isBusinessContact' in a relation, $\rho_{isBusinessContact/isFriend}$(addressBook) might be used.

Natural join is a binary operator that is written as (R⋈S) where R and S are relations. The result of the natural join is the set of all combinations of rows in R and S that are equal on their common attribute names. The natural join is arguably one of the most important operators since it is the relational counterpart of logical AND. More formally the semantics of the natural join are defined as follows: R⋈S={t∪s|t∈R∧ s∈S∧ Fun(t∪s)} where Fun is a predicate that is true for a table R if and only if it is also true for relation s. Where f(t,s) is true for the tuples t and s. It is usually required that R and S must have at least one common attribute.

Cartesian product is an operation that joins two tables without restriction by any criteria, resulting in every row of the first table being matched with every row of the second table. In mathematics, a Cartesian product is a mathematical operation which returns a set (or product set or simply product) from multiple sets. That is, for sets A and B, the Cartesian product A×B is the set of all ordered pairs (a,b) where a∈A and b∈B. Products can be specified using set-builder notation, e.g. A×B={(a,b)| a∈A and b∈B}.

The relational algebra primitives described above can be implemented on DNA molecules that make up a relational DNA digital data storage by performing certain molecular biology techniques on the DNA which are referred to herein as DNA-manipulation primitives.

FIG. 1 shows an illustrative architecture 100 for implementing and interacting with a DNA digital data storage. User 102 interacts with a digital computer 104 to provide instructions to the DNA DBMS and to receive information from the DNA digital data storage. As used herein, "digital computer" means a computing device including at least one hardware microprocessor and memory capable of storing information in a binary format. The digital computer 104 may be a desktop computer, notebook computer, tablet computer, game console, a mobile computer, a smartphone, or the like. The digital computer 104 may include one or more input/output components(s) such as a keyboard, a pointing device, a touchscreen, a microphone, a camera, a display, a speaker, a printer, and the like.

The memory of the digital computer 104 may include removable storage, non-removable storage, local storage, and/or remote storage to provide storage of computer readable instructions, data structures, program modules, and other data. The memory may be implemented as computer-readable media. Computer-readable media includes, at least, two types of media, namely computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer readable instructions, data structures, program modules, or other data in a modulated data signal, such as a carrier wave, or other transmission mechanism. As defined herein, computer-readable storage media and communications media are mutually exclusive.

Digital computer 104 may include a user interface that is similar to a user interface used for interacting with conventional, relational databases stored entirely in electronic form. In one implementation, a communications network 106 provides a communication path for information between the digital computer 104, one or more network computers 108, and an automated system 110 that manipulates the DNA molecules in the DNA digital data storage. The one or more network computers 108 may be a server computer, a collection of server computers such as a server farm, a cloud computing system that uses processing power, memory, and other hardware resources distributed across multiple geographic locations, or the like. The network 106 may be implemented as any type of communications network such as a local area network, a wide area network, a mesh network, and ad hoc network, a peer-to-peer network, the Internet, a cable network, a telephone network, and the like. In one implementation, the digital computer 104 may have a direct connection to the automated system 110 without the presence of an intervening network. The direct connection may be implemented as a wired connection or a wireless connection. A wired connection may include one or more wires or cables physically connecting the digital computer 104 to the automated system 110. For example, the wired connection may be created by a headphone cable, a telephone cable, a SCSI cable, a USB cable, an Ethernet cable, or the like. The wireless connection may be created by radio frequency (e.g., any version of Bluetooth, ANT, Wi-Fi IEEE 802.11, etc.), infrared light, or the like.

The automated system 110 may be controlled by controller 112 that is connected to network 106 or connected directly to the digital computer 104. Controller 112 receives a series of instructions for manipulating the DNA molecules. The instructions may correspond to one or more relational algebra operations. The digital computer 104 and/or the network computers 108 may receive a relational algebra operation (e.g., from the user 102 or another computer) and translate the relational algebra operation into the series of instructions for manipulating the DNA molecules. The controller 112 can communicate the sequence of instructions to the specific hardware and devices that comprise the automated system 110.

In one implementation, the automated system 110 is a microfluidics system. Microfluidics is a multidisciplinary field intersecting engineering, physics, chemistry, biochemistry, nanotechnology, and biotechnology, with practical applications to the design of systems in which small volumes of fluids will be handled. Typically, fluids are moved, mixed, separated, or otherwise processed. Numerous applications employ passive fluid control techniques like capillary forces. In some applications, external actuation is additionally used for a directed transport of the media. Examples of external actuation include rotary drives applying centrifugal forces for the fluid transport on the passive chips. Active microfluidics refers to the defined manipulation of the working fluid by active (micro) components such as micropumps or micro valves. Micro pumps supply fluids in a continuous manner or are used for dosing. Micro valves determine the flow direction or the mode of movement of pumped liquids. Often processes which are normally carried out in a lab are miniaturized on a single chip in order to enhance efficiency and mobility as well as reducing sample and reagent volumes. As used herein, the automated system 110 includes other equipment for manipulating DNA. For example, an oligonucleotide synthesizer, a DNA sequencer, a flow cytometry, and the like may also be part of the automated system 110. The oligonucleotide synthesizer may be configured to synthesize DNA molecules complementary to all or part of one of the DNA molecules 116 present in the DNA digital data storage. The DNA sequencer may be configured to sequence all or part of one of DNA molecules 116 and provide the sequence to the digital computer 104.

The term "oligonucleotide" as used herein is defined as a molecule including two or more nucleotides. Oligonucleotides include probes and primers. Oligonucleotides used as probes or primers may also include nucleotide analogues such as phosphorothioates, alkylphosphorothioates, peptide nucleic acids, or intercalating agents. The introduction of these modifications may be advantageous in order to positively influence characteristics such as hybridization kinetics, reversibility of the hybrid-formation, stability of the oligonucleotide molecules, and the like.

The automated system 110 includes a structure, such at least one chamber 114 which holds the DNA molecules 116. The DNA molecules 116 may be present in a liquid suspension, a glassy (or vitreous) state, as lyophilized product, or other format. The structure, such as chamber 114, may be implemented as any type of mechanical, biological, or chemical arrangement which holds a volume of liquid including DNA to a physical location. For example, a single flat surface having a droplet present thereon, with the droplet held in part by surface tension of the liquid, even though not fully enclosed within a container, is one implementation of the chamber 114. The DNA 116 present in the chamber 114 and present in the DNA digital data storage may be single-stranded DNA (ssDNA), double-stranded DNA (dsDNA), or a combination.

The automated system 110 may perform many types of manipulations on the DNA digital data storage and/or selected DNA molecules. The automated system 110 may be referred to as a DNA DBMS. For example, the automated system 110 may be configured to move a volume of liquid from the chamber 114 to another chamber in response to a series of instructions from the controller 112. One type of manipulation is sample partitioning. Numerous methods can be used to divide samples into discrete partitions (e.g., droplets). Examples of partitioning methods and systems include use of one or more of emulsification, droplet actuation, microfluidics platforms, continuous-flow microfluidics, reagent immobilization, and combinations thereof. In some embodiments, partitioning is performed to divide a sample into a sufficient number of partitions such that each partition contains one or zero nucleic acid molecules. In some embodiments, the number and size of partitions is based on the concentration and volume of the bulk sample.

Microfluidics systems and methods to divide a bulk volume into partitions include emulsification, generation of "water-in-oil" droplets, and generation of monodisperse droplets as well as using channels, valves, and pumps. Partitioning methods can be augmented with droplet manipulation techniques, including electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). In some embodiments, a droplet microactuator is supplemented with a microfluidics platform (e.g. continuous flow components). Some implementations of microfluidics systems use a droplet microactuator. A droplet microactuator can be capable of effecting droplet manipulation and/or operations, such as dispensing, splitting, transporting, merging, mixing, agitating, and the like.

Amplification of a number of copies of a DNA molecule is an additional example of a manipulation that can be performed by the automated system 110. Any of several methods can be used to amplify a target nucleic acid from a sample. The term "amplifying" which typically refers to an "exponential" increase in the number of copies of the target nucleic acid is used herein to describe both linear and exponential increases in the numbers of a select target sequence of nucleic acid. The term "amplification reaction mixture" refers to an aqueous solution comprising the various reagents used to amplify a target nucleic acid. These include enzymes, including, polymerases, and thermostable polymerases such as DNA polymerase, RNA polymerase and reverse transcriptase, aqueous buffers, salts, amplification primers, target nucleic acid, and nucleoside triphosphates. Depending upon the context, the mixture can be either a complete or incomplete amplification reaction mixture. The method used to amplify the target nucleic acid can be any method available to one of skill in the art. Any in vitro means for multiplying the copies of a target sequence of nucleic acid can be utilized. These include linear, logarithmic, or any other amplification method. Illustrative methods include polymerase chain reaction (PCR), isothermal procedures (using one or more RNA polymerases, strand displacement, partial destruction of primer molecules), ligase chain reaction (LCR), Qβ RNA replicase systems, RNA transcription-based systems (e.g., TAS, 3SR), rolling circle amplification (RCA), and strand displacement amplification (SDA), among others. Many systems are suitable for use in amplifying target nucleic acids as would be understood by one of skill in the art.

A variety of PCR techniques are known and can be used in the assays described herein. PCR techniques are typically used for the amplification of at least a portion of an oligonucleotide. The sample to be tested for the presence of an analyte-specific sequence is contacted with the first and second oligonucleotide primers; a nucleic acid polymerase; and nucleotide triphosphates corresponding to the nucleotides to be added during PCR. The natural base nucleotide triphosphates include dATP, dCTP, dGTP, dTTP, and dUTP. Nucleoside triphosphates of non-standard bases can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

An additional type of PCR is Droplet Digital™ PCR (ddPCR™) (Bio-Rad Laboratories, Hercules, Calif.). ddPCR technology uses a combination of microfluidics and surfactant chemistry to divide PCR samples into water-in-oil droplets. The droplets support PCR amplification of the target template molecules they contain and use reagents and workflows similar to those used for most standard Taqman probe-based assays. Following PCR, each droplet is analyzed or read in a flow cytometer to determine the fraction of PCR-positive droplets in the original sample. These data are then analyzed using Poisson statistics to determine the target concentration in the original sample. See Bio-Rad Droplet Digital™ (ddPCR™) PCR Technology.

While ddPCR™ is a one spdPCR approach, other sample partition PCR methods based on the same underlying principles may also be used. The partitioned nucleic acids of a sample can be amplified by any suitable PCR methodology that can be practiced within spdPCR. Illustrative PCR types include allele-specific PCR, assembly PCR, asymmetric PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap-extension PCR, polymerase cycling assembly, qualitative PCR, quantitative PCR, real-time PCR, single-cell PCR, solid-phase PCR, thermal asymmetric interlaced PCR, touchdown PCR, universal fast walking PCR, etc. Ligase chain reaction (LCR) may also be used.

The automated system 110 may perform techniques to determine if a given sequence exists in the DNA digital data storage without sequencing. Techniques for determining if a given sequence exists in a DNA digital data storage include in situ hybridization (ISH), molecular beacons, nucleic acid sequence-based amplification (NASBA), strand displacement amplification (SDA), loop-mediated amplification (LAMP), the invader assay, the rolling circle amplification (RCA), recombinase polymerase amplification (RPA), nicking endonuclease signal amplification (NESA)/nicking endonuclease assisted nanoparticle activation (NEANA), exonuclease III-aided target recycling approach, junction or Y probes, catalytic beacons based on reactivation of enzymatic activity, template directed chemical reactions, and non-covalent DNA catalytic reactions, hybridization chain reactions (HCR) each of which is well understood by those having ordinary skill in the art.

Many such techniques use a fluorescently labeled probe that creates a detectable signal with the probe hybridizes to homologous DNA. Illustrative types of probe technology includes fluorescent energy transfer, fluorescent resonance energy transfer, contact quenching, fluorescence nucleic acid hybridization probes, adjacent probes, 5'-nuclease probes, molecular beacon probes, strand-displacement probes, as well as other types of probe technology as is understood by those of ordinary skill. Thus, presence of a given table-ID, field-ID, data value, etc. may be determined without the need for sequencing and analysis on a digital computer. Multiple types of fluorescent probes exist making it possible query a DNA digital data storage for multiple different matching DNA sequences simultaneously such as, for example, by using a first colored fluorescent probe to query for table-ID and a second colored fluorescent probe to query for field-ID. Strength of a signal generated by a fluorescent probe may also be used to approximate the number of matches in the DNA digital data store to determine, for example, whether a first data value (e.g., last name=Smith) is more or less common than a second data value (e.g., last name=Jones).

The network computers 108 may provide database management software that generates the user interface for display on the digital computer 104. In this implementation, most or all of the processing of electronic information may be performed by the network computers 108 and the digital computer 104 may serve as a thin client or terminal that merely provides output device and input device functionality to the user 102. In one implementation, the digital computer 104 and/or the network computers 108 may maintain a correspondence between relational database operations and DNA-manipulation primitives. Upon receiving instructions to perform one or more relational database operations, the network computers 108 may translate those operations into a series of DNA-manipulation primitives that are passed to the controller 112. In one implementation, the network computers 108 may be omitted and some or all of their functionality may be performed by the digital computer 104.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations may be modified or omitted.

Figure 2:
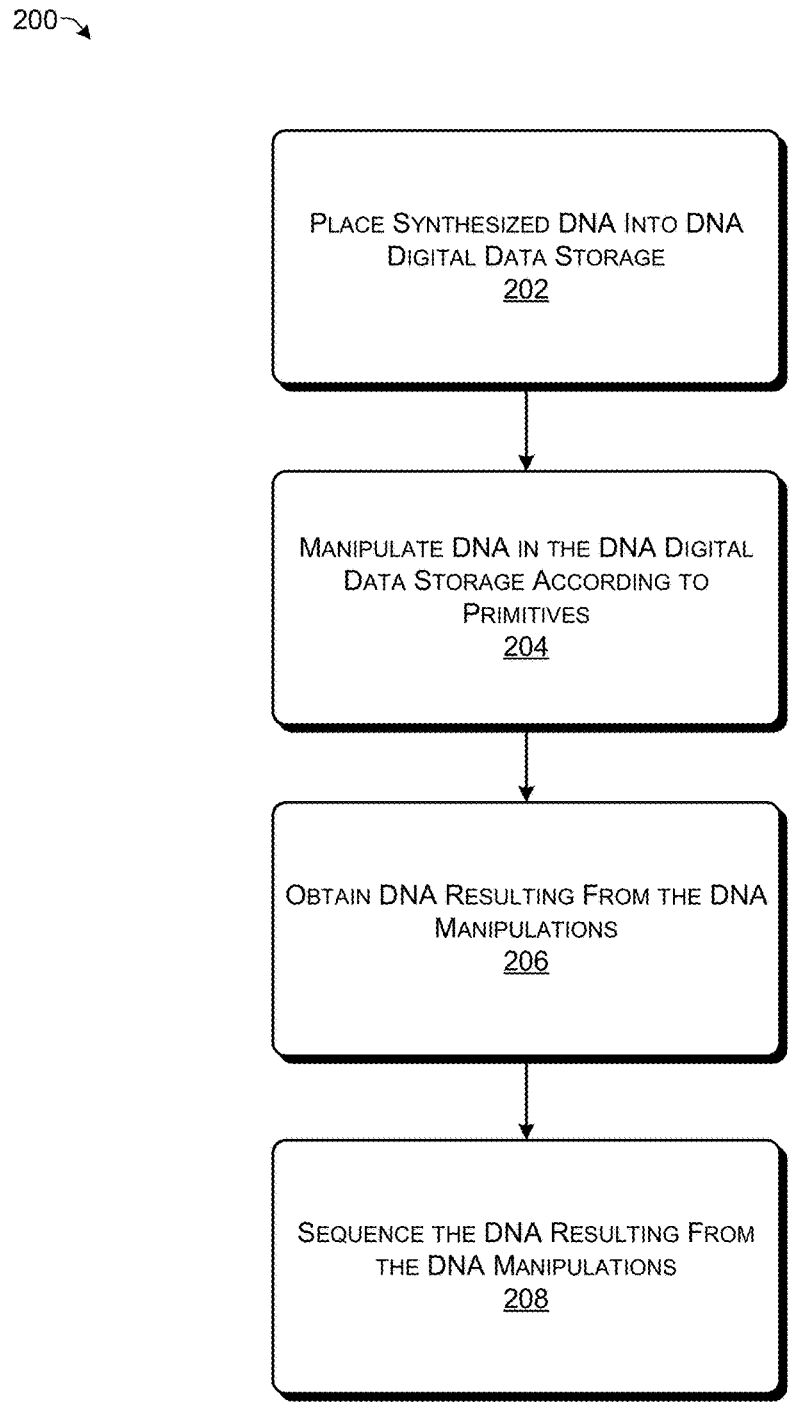
FIG. 2 shows an illustrative process for operating a DNA digital data storage.

FIG. 2 shows process 200 for interacting with a DNA digital data storage. The process 200 may be implemented by the architecture 100 shown in FIG. 1.

At 202, synthesized DNA is placed into a DNA digital data storage. Sequences of DNA molecules may be specifically designed for storage and organization of information. The DNA molecules may then be synthesized according to this design. One having ordinary skill in the art can select an appropriate technology and technique for oligonucleotide synthesis in order to create a DNA molecule having an arbitrary and predesigned sequence. Synthesizing DNA may create thousands or millions, or more individual molecules that each encode information within the DNA digital data storage. In one implementation, each molecule represents a row of a table. All of the molecules that make up a given DNA digital data storage may be placed in the same chamber. Alternatively, a DNA digital data storage may be physically separated into multiple chambers. One arrangement for separating a DNA digital data storage into multiple chambers is to place the DNA molecules corresponding to each individual table in a separate chamber. Although in some examples a DNA digital data storage is discussed as containing only one table, it is to be understood that a DNA digital data storage may also include multiple tables without changing the principles described herein.

At 204, the DNA in the DNA digital data storage is manipulated according to DNA-manipulation primitives. In one implementation the DNA may be stored in a first form (e.g., dried, lyophilized, etc.) then converted to a second form (e.g., aqueous solution) prior to manipulation. In an implementation, some or all of the DNA molecules may be replicated by PCR or other technique. One set of copies of the replicated DNA molecules may be returned to the first form for storage and another copy of the replicated DNA molecules may be used as the target for the DNA-manipulation primitives. As described in detail below, the DNA-manipulation primitives may include such things as separating the DNA from a chamber into two separate chambers according to characteristics of the DNA molecules, performing PCR to amplify selected portions of the DNA molecules, combine the DNA molecules from separate chambers into a single chamber, and the like. The DNA-manipulation primitives may be provided to the controller 112 by the network computers 108 and/or the digital computer 104.

At 206, a DNA resulting from the DNA manipulations at 204 is obtained from the DNA digital data storage. This DNA represents DNA molecules that were identified in the DNA digital data storage by implementing the DNA-manipulation primitives at 204. Use of the DNA-manipulation primitives can perform part or all of a relational algebra operation on the DNA digital data storage. By limiting the number of DNA molecules that need to be analyzed in order to fully implement the relational algebra operation, the length of DNA that is sequenced is shorter, and any further processing that occurs on information in electronic form is made more efficient because the amount of information that must be processed has already been reduced through DNA manipulations. Additionally, manipulating the DNA as DNA, rather than first converting to electronic information then manipulating, can take advantage of properties of DNA computation such as massive parallelism. DNA sequencing may also be performed in parallel prior to sorting the DNA molecules. If sorting is needed it may be performed by a digital computer on the sequencing output.

At 208, the DNA obtained at 206 is sequenced. Any technique for sequencing nucleic acids known to those skilled in the art can be used. DNA sequencing techniques include classic dideoxy sequencing reactions (Sanger method) using labeled terminators or primers and gel separation in slab or capillary electrophoresis. In one implementation, next generation (NextGen) sequencing platforms are advantageously used in the practice of the invention. NextGen sequencing refers to any of a number of post-classic Sanger type sequencing methods which are capable of high throughput, multiplex sequencing of large numbers of samples simultaneously. Current NextGen sequencing platforms are capable of generating reads from multiple distinct nucleic acids in the same sequencing run. Throughput is varied, with 100 million bases to 600 giga bases per run, and throughput is rapidly increasing due to improvements in technology. The principle of operation of different NextGen sequencing platforms is also varied and can include: sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real-time monitoring of the incorporation of labeled nucleotides during a polymerization step, polony sequencing, single molecule real-time sequencing, nanopore sequencing, and SOLiD sequencing.

454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

A sequencing technique that can be used is Helicos True Single Molecule Sequencing (tSMS). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm². The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step.

Another example of a DNA sequencing technique that can be used is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide.

Another example of a sequencing technology that can be used is SOLEXA sequencing (Illumina). SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection, and identification steps are repeated.

Another example of a sequencing technology that can be used includes the single molecule, real-time (SMRT™) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off Detection of the corresponding fluorescence of the dye indicates which base was incorporated. The process is repeated.

Another example of a sequencing technique that can be used is nanopore sequencing. A nanopore is a small hole, of the order of 1 nanometer in diameter Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used involves using a chemical-sensitive field effect transistor (chemFET) array to sequence DNA. In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used involves using an electron microscope. In one example of the technique, individual DNA molecules are labeled using metallic labels that are distinguishable using an electron microscope. These molecules are then stretched on a flat surface and imaged using an electron microscope to measure sequences.

The electronic information generated by sequencing can be sent from the system 110 to the network computers 108 and/or the digital computer 104 for further manipulation in digital form and also for presentation on a user interface to the user 102.

Figure 3:
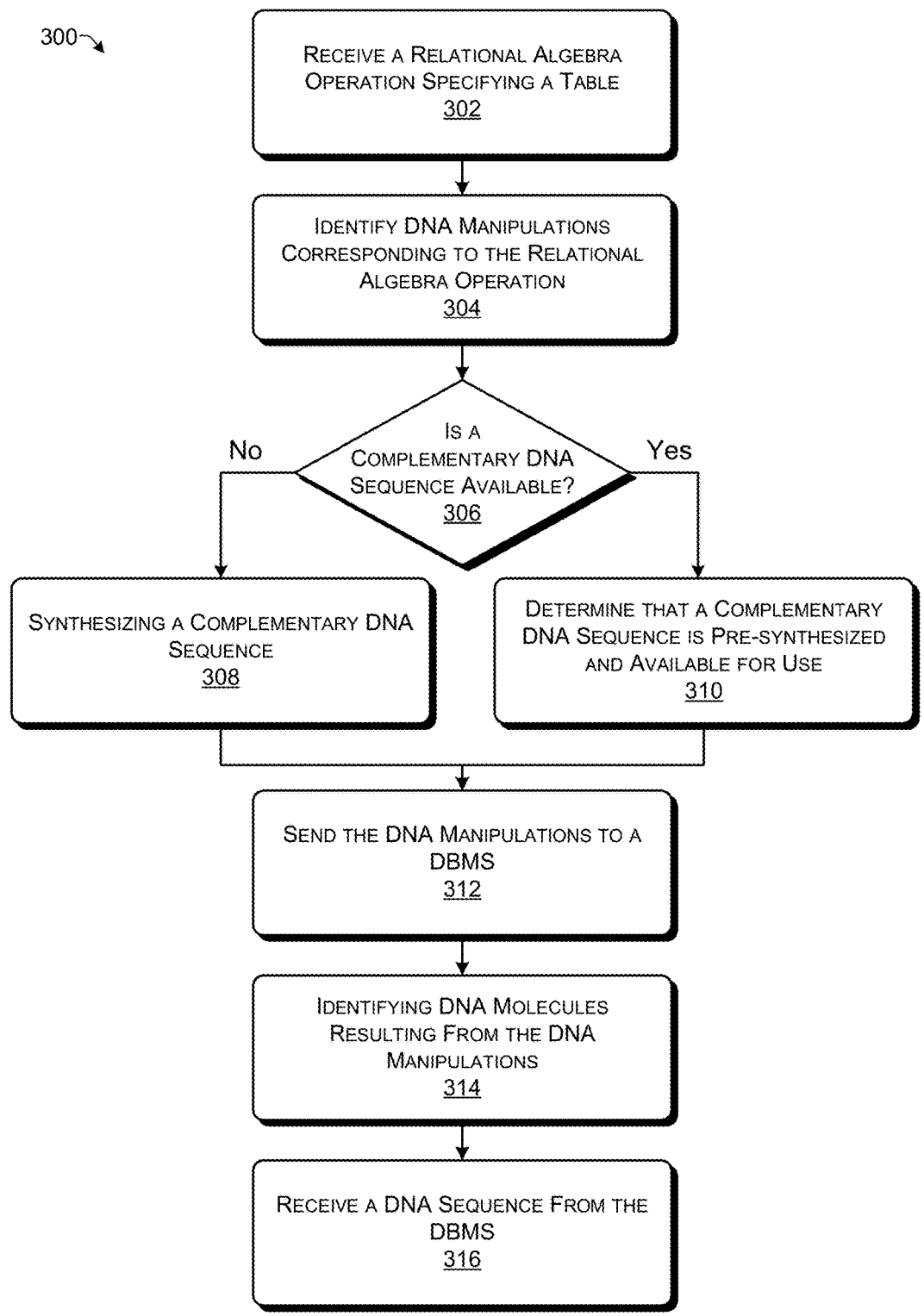
FIG. 3 shows an illustrative process for interacting with a DNA digital data storage.

FIG. 3 shows process 300 for interacting with a DNA digital data storage. The process 300 may be implemented by any combination of the digital computer 104, the network computers 108, and the controller 112 shown in FIG. 1.

At 302, a relational algebra operation specifying a table in a relational database is received. The table is designated by a table-ID sequence. The table-ID sequence is a DNA sequence in a strand of DNA that uniquely identifies a table within a relational database. Specifically, the table-ID sequence is a series of DNA bases that provides a unique identifier. Each strand of DNA that belongs to a given table may be labeled with the same table ID. A relational database that contains many tables when implemented as a DNA digital data storage will contain multiple DNA molecules associated with respective ones of the multiple different tables. Each of the DNA molecules may include a table-ID sequence identifying the table associated with the information encoded in that particular DNA molecule.

At 304, DNA manipulations corresponding to the relational algebra operation are identified. The DNA manipulations include hybridizing a complementary DNA sequence to at least a portion of the table-ID sequence included in a DNA strand. Other DNA manipulations include adding DNA to a chamber, moving DNA from a chamber, combining DNA from two or more separate chambers into a single chamber, attaching a DNA molecule to a solid support, removing a DNA molecule from a solid support, synthesis of DNA, sequencing of DNA, amplification of a known sequence of DNA, removing a region of DNA flanked by known sequences, and replacing a portion of pre-defined DNA with another DNA sequence. These manipulations may be performed manually or by a mechanized technique such as automated system 110.

At 306 the availability of a complementary DNA sequence is determined.

If a complementary DNA sequence is not already available, process 300 proceeds to 308 and a DNA sequence complementary to the table-ID sequence is synthesized. This complementary sequence may be synthesized by any technique known to those of skill in the art. Once the complementary DNA sequence is available, it may be used to query the DNA digital data storage to identify all DNA molecules that include the table-ID sequence. Synthesizing the complementary sequence in response to instructions from a digital computer may cause latency due to the time needed to generate the new DNA sequence. However, this technique provides flexibility because there are no restrictions on the sequence that is generated.

Alternatively, at 310, it is determined that the DNA sequence complementary to the table-ID sequence is pre-synthesized and available for use to query the DNA digital data storage. Pre-synthesized DNA molecules may be stored in a separate chamber, attached to a solid support such as a gene chip or available in some other format. DNA molecules may be pre-synthesized because they were used in a prior query, they may be pre-synthesized as part of creation of a DNA digital data storage, or pre-synthesized for another reason. Records of which molecules have been pre-synthesized may be stored in electronic form so that available, pre-sequenced DNA molecules are easily searchable by the digital computer 104 and/or the network computers 108. If it is determined that the complementary sequence for the table-ID sequence already exists because of pre-synthesis, the existing molecules may be used to query the DNA digital data storage without waiting for a new DNA molecule to be synthesized. This technique has the advantage of improved speed, but is limited to only those DNA molecules that have already been pre-synthesized.

At 312, instructions to perform the DNA manipulations are sent to an automated system 110 that implements the manipulations on the DNA digital data storage. In one implementation, some or all of the instructions may be sent from the DBMS to a controller which controls an automated system that acts on the DNA digital data storage. In one implementation, some or all of the DNA manipulations may be implemented by human operators working with equipment to effect the DNA manipulations. Multiple operations may be combined to create a single (or several) DNA manipulations. The order of operations performed for a DNA manipulation may be changed and optimized.

At 314, DNA molecules resulting from the DNA manipulations on the DNA digital data storage are identified. The DNA molecules may be identified, for example, by using physical properties of the DNA molecules to separate them into a separate chamber from other DNA molecules in the DNA digital data storage. The DNA molecules may be identified based on the DNA manipulations performed at 310. The identified DNA molecules may represent those DNA molecules that encode information pertinent to the relational algebra operation received at 302.

At 316, a DNA sequence is received from the DBMS. The DNA sequence may be generated by a DNA sequencer. The DNA sequence is electronic data, such as an electronic file, that contains a series of representations of DNA bases such as the letters A, G, C, and T. In one implementation, this DNA sequence may include sequences only of the DNA molecules identified at 312, thus, saving the time and effort of sequencing a larger portion of the DNA molecules from the DNA digital data storage. The electronic file may be provided to the digital computer 104 and/or the network computers 108. Information contained in the electronic file may be further processed to fully implement a relational algebra operation. Additionally or alternatively information from the electronic file may be converted into a different format for rendering on a user interface and presentation to a user. For example, a sequence of DNA bases may be converted into a passage of English language text that is presented to the user 102 on a user interface of the digital computer 104.

Illustrative DNA Molecules

Figure 4:
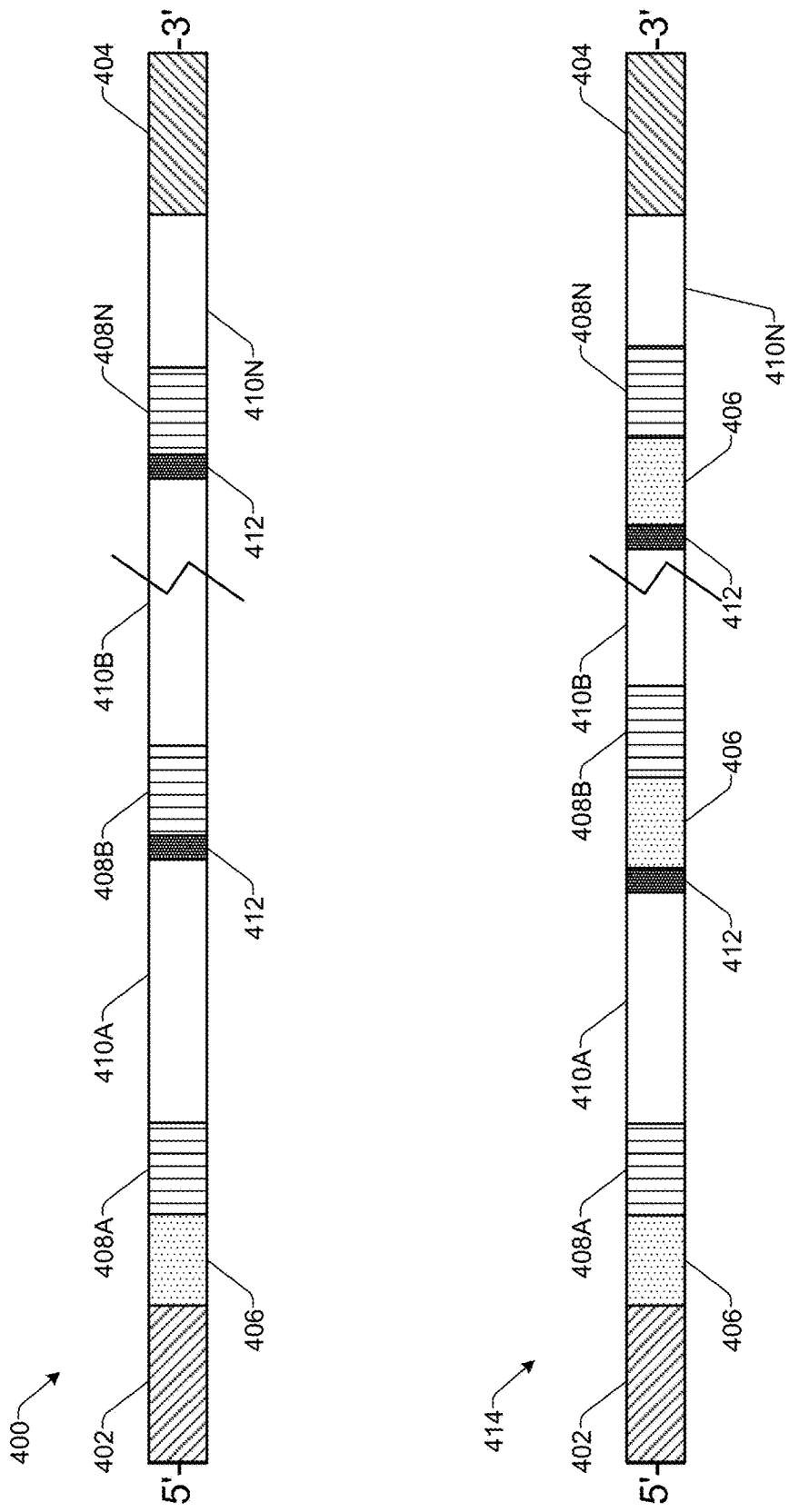
FIG. 4 shows illustrative configurations of information regions on DNA molecules usable in a DNA digital data storage.

FIG. 4 shows two example configurations of DNA molecules that may be present in a DNA digital data storage. Schematic 400 illustrates a section of ssDNA having a plurality of regions. The ssDNA may be present in the DNA digital data storage as a single-stranded molecule or may hybridize to a complementary ssDNA molecule to form dsDNA. A 5'-end sequence 402 is located on the 5' end of the ssDNA molecule. The 5'-end sequence 402 is a predefined sequence that facilitates manipulation of the ssDNA molecule. In one implementation the 5'-end sequence 402 includes one or more known primer sites. Similarly, a 3'-end sequence 404 is present on the 3' end of the ssDNA molecule. The 3'-end sequence 404 is a predefined sequence that may also facilitate manipulation of the ssDNA molecule. In one implementation the 3'-end sequence 404 includes one or more known primer sites. In one implementation the 5'-end sequence 402 and/or the 3'-end sequence 404 may include Gibson assembly sites. The presence of Gibson assembly sites may facilitate end-to-end joining of DNA molecules (e.g., table rows). For example, certain DNA molecules may contain portions of the end sequences that are complementary to end sequences of other DNA molecules. The Gibson assembly sites may be designed to be unique from other sequences in the DNA digital data storage, for example, by including synthetic nucleotides. In one implementation the 5'-end sequence 402 and/or the 3'-end sequence 404 may include known restriction sites. In one implementation the 5'-end sequence 402 and/or the 3'-end sequence 404 may include promoter binding sites and stop codons to control translation of RNA molecules made from the DNA. In one implementation, the 5'-end sequence 402 and/or the 3'-end sequence 404 may include hairpin forming sequences. In one implementation, the 5'-end sequence and/or the 3'-end sequence 404 may serve only structural purposes such as, for example, providing separation between DNA that encodes information and the ends of the DNA molecule. The 5'-end sequence 402 and/or the 3'-end sequences 404 may be omitted and added at later times or as needed by ligation.

The term "primer" as used herein refers to an oligonucleotide which is capable of acting as a point of initiation of nucleic acid synthesis when placed under conditions in which synthesis of a primer product which is complementary to a nucleic acid strand is induced, i.e., in the presence of four different nucleotide triphosphates with appropriate enzymes at a suitable temperature and salt concentration. Specific length and sequence will depend on the complexity of the required DNA targets, as well as on the conditions of primer use such as temperature and ionic strength. In some implementations, a primer can be 5-50 nucleotides, 10-25 nucleotides, or 15-20 nucleotides in length. The fact that amplification primers do not have to match exactly with the corresponding template sequence to warrant proper amplification is amply documented in the literature.

An additional region that may be included in DNA molecules in a DNA digital data storage is a table-ID region 406 that identifies a table in the DNA digital data storage. The data included in a given table may be stored in many hundreds or thousands of separate DNA molecules. By including a table-ID region 406 in each DNA molecule that encodes information for a given table it is possible to find the information included within a selected table. The table IDs may be designed so that each is sufficiently different from the others to prevent non-specific annealing under the conditions used to manipulate the DNA digital data storage. In one implementation each DNA molecule is associated with one and only one table. Further, in one implementation each DNA molecule encodes information for one and only one row of a table. If the amount of information present in one row of a table exceeds the amount of information that can be stored in one DNA molecule, the information from a single row may be split across two or more DNA molecules. As discussed above, the table-ID region 406 may be any arbitrary sequence of DNA bases that uniquely identifies a given table. The table-ID region 406 is shown in schematic 400 as adjacent to the 5'-end sequence 402, but the table-ID region 406 may be located anywhere along the DNA molecule.

Field-ID regions 408A, 408B, . . . 408N (collectively 408) identify specific fields within a table. Like the table-ID region 406, the field-ID region 408 may be an arbitrary sequence of DNA bases that uniquely identifies the field. A field-ID region 408 may be shared across DNA molecules within different tables. For example, if the field is "phone number" that field may be present in a table of employee information and present in a table containing department contact information. Of course, values for individual entries (i.e., the phone numbers) within that field will likely be different. A single DNA molecule may contain information from multiple fields, and thus, there may be multiple field-ID regions 408A, 408B, . . . 408N. The field IDs may be designed so that each is sufficiently different from the others, and from the table IDs, to prevent non-specific annealing under the conditions used to manipulate the DNA digital data storage. The combination of the table-ID region 406 and the field-ID region 408 allows for identification of a specific field of a given table. By designing the DNA digital data storage such that each row of a table is represented by a DNA molecule, the DNA molecule provides the row, the field-ID 408 provides the column, and the table-ID 106 identifies the table. In some implementations, field-ID regions 408 may be omitted.

The field-ID region 408 is associated with a data region 410. The data region 410 represents the data stored in the table. Thus, the data region 410 may contain the value for a given entry in the table rather than information used for management of the DNA digital data storage. The information is encoded as a series of DNA bases, but may represent any type of data such as text, audio files, video files, or anything else that may be encoded by conventional binary data recording in electronic computers. For some tables, the information contained in the data region 410 may be metadata that is used to manage the DNA digital data storage. The various regions of the DNA molecule shown in FIG. 4 are not to scale. The data region 410 may be longer, that is include a greater number of DNA bases, than any of the other regions. Each of the multiple field-ID regions 408A, 408B, . . . 408N, may be associated with respective data regions 410A, 410B, . . . 410N. As shown in the schematic 400, field-ID regions 408A, 408B, . . . 408N may be associated with respective data regions 410A, 410B, . . . 410N by locating the field-ID region 408 adjacent to the associated data region 410.

Two data regions such as, for example, data regions 410A and 410B may be separated by a pre-defined separator 412. The same pre-defined separator 412 may be present between each instance of a data region 410 and any neighboring data region. In one implementation the pre-defined separator 412 may include metadata for an associated (e.g., adjacent) data region 410. In one implementation, a data region 410 may contain a row-ID that is unique within a database for a given row. The row-ID could be one or more columns that uniquely identify the row from other rows present in the tables of a database. It is not necessary for a row to have a row-ID (i.e., a table may have duplicate rows).

Schematic 414 illustrates a different arrangement of regions on a section of DNA. Schematic 414 differs from schematic 400 in that a separate instance of the table-ID region 406 is included adjacent to each data region 410A, 410B, . . . 410N. Although FIG. 4 shows two arrangements of regions within DNA molecules, one of ordinary skill in the art will appreciate that other arrangements of the respective regions are possible.

A single DNA molecule may encode less or more than a single row or only a portion of a table. A single DNA molecule may encode an entire table, multiple tables, an entire database (i.e., all the tables that comprise a given database), or multiple databases. A DNA molecule encoding an entire table may include pre-defined row separators between segments of the DNA molecule that encode different rows of the DNA molecule. The pre-defined row separators mark the change from one row to another row. In implementations in which a single DNA molecule encodes an entire database, the DNA molecule may include pre-defined table separators between segments of the DNA molecule that encode different tables. The pre-defined table separators mark the points in the DNA molecule when the encoded information changes from one table to another table. Similarly, a DNA molecule encoding multiple databases may include pre-defined database separators that separate the portions of the DNA molecule encoding different databases from each other. Each of the pre-defined separators (row, table, and database) may include known restriction enzyme sites for separating the single DNA molecule into multiple DNA molecules. In an implementation, all of the pre-defined row separators may have the same restriction enzyme site enabling separation of the single DNA molecule into separate DNA molecules each containing information for one of the rows of the table. The restriction enzyme sites in the pre-defined row separators may be selected so that those same restriction enzyme sites are not found anywhere else in the DNA molecule. Similarly, the pre-defined table and database separators may contain restriction enzyme sites that are unique to those respective separators. Additionally, the restriction enzyme sites for pre-defined row separators may be different for each table within a DNA molecule containing multiple tables. Similarly, the restriction enzyme sites for pre-defined table separators may be different for each database within a DNA molecule containing multiple databases.

Illustrative DNA-Manipulation Primitives

FIGS. 5-11 show several basic DNA manipulation operations, or DNA manipulation primitives, on which the relational operators can be implemented. These specific operations are both sufficient to express the relational algebra and have the performance and scale qualities that the operations can be implemented efficiently on DNA.

Figure 5A:
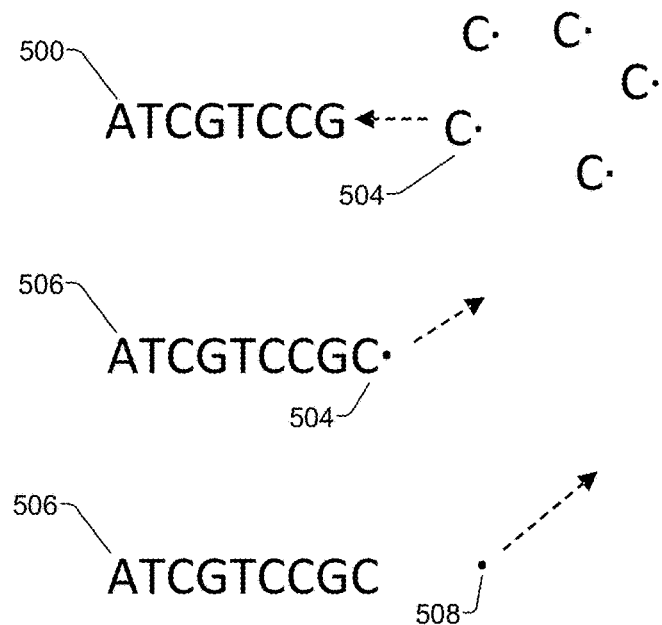
FIGS. 5A and 5B show techniques for synthesizing DNA molecules.

FIG. 5A shows chemical synthesis of a ssDNA molecule. Chemical synthesis proceeds by building a ssDNA molecule 500 through addition of individual triphosphate nucleotide bases 504 to create a longer ssDNA molecule 506 and a diphosphate 508. DNA molecules can be synthesized chemically, for instance by the conventional phospho-triester method. An oligonucleotide synthesizer may be used to synthesize DNA molecules complementary to a sequence of a table-ID region, a field-ID region, or any other region of a DNA molecule present in a DNA digital data storage. A number of methods for DNA synthesis and commercial oligonucleotide synthesizers are available. Methods for DNA synthesis include solid-phase phosphoramidite synthesis, microchip-based oligonucleotide synthesis, ligation-mediated assembly, PCR-mediated assembly, and the like. For example, such synthesis can be performed using an ABI 394 DNA Synthesizer (Applied Biosystems, Foster City, Calif.) in 0.2 µmol scale followed by standard cleavage and deprotection protocol, e.g., using 28% aqueous ammonia or a 3:1 solution of ammonia in methanol. One having ordinary skill in the art can select other cleaving agents, such as methylamine, to be used instead of, or in addition to, ammonia, if desired.

Figure 5B:
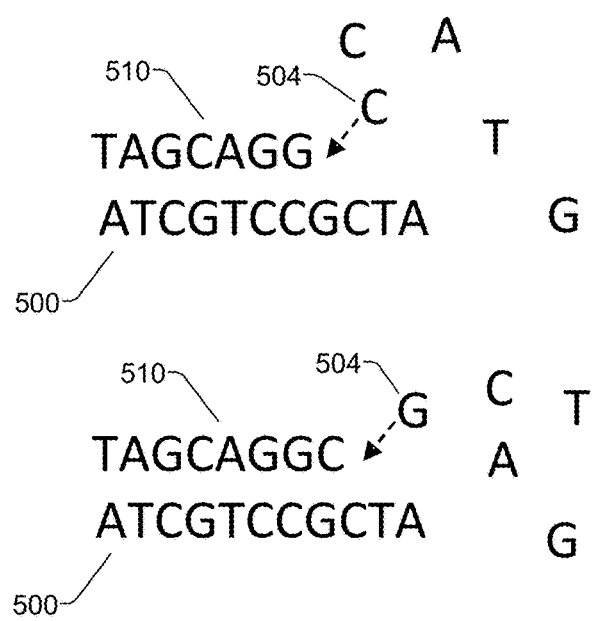

FIG. 5B shows DNA synthesis by PCR amplification that creates a copy of an original ssDNA molecule 500 by addition of individual nucleotide bases 504 to a growing ssDNA molecule 510 that is complementary and hybridized to the original ssDNA molecule 500. Sequential addition of complementary nucleotide bases 504 creates a dsDNA molecule. DNA molecules can also be synthesized by any appropriate technique including the cloning of recombinant plasmids containing inserts including the corresponding nucleotide sequences, if need be by cleaving the latter out from the cloned plasmids upon using the adequate nucleases and recovering them, e.g. by fractionation according to molecular weight.

Figure 6A:
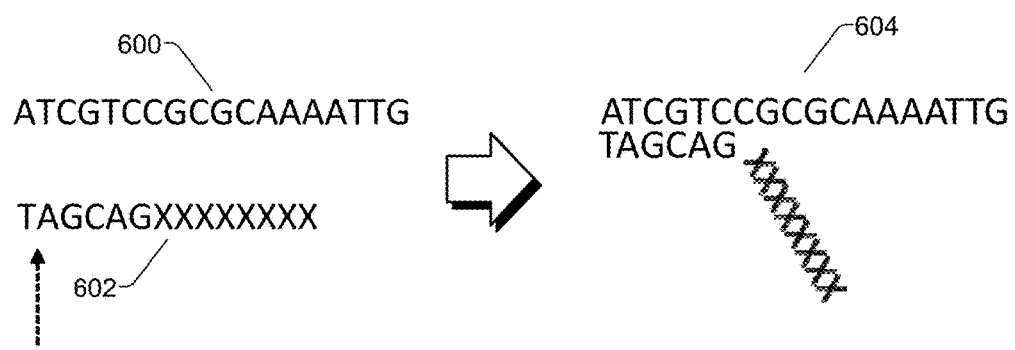
FIGS. 6A and 6B show hybridization and denaturation of complementary DNA molecules.

FIG. 6A shows a representation of DNA hybridization. "Hybridizing" as used herein means placing two complementary ssDNA molecules in conditions that allow hybridization to form a dsDNA molecule or causing two complementary ssDNA molecules to hybridize and form a dsDNA molecule. Hybridization may be performed under high stringency conditions. High stringency conditions include, for example, 2 h to 4 days incubation at 42° C. using a DIG-labeled DNA probe (prepared by, e.g., using a DIG labeling system; Roche Diagnostics GmbH, 68298 Mannheim, Germany) in a solution such as DigEasyHyb solution (Roche Diagnostics GmbH) or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C. Here, a partial hybridization between the first ssDNA molecule 500 and a second ssDNA molecule 602 creates a partially hybridized molecule 604. The complementary base pairs hybridize to each other while the non-complementary base pairs represented by X do not hybridize to each other. In one implementation, the ssDNA molecule 602 may be a probe that is used to identify ssDNA molecules such as molecule 600 which includes a complementary sequence. The term "probe" refers to single-stranded sequence-specific oligonucleotides which have a sequence that is complementary to a target oligonucleotide sequence (target) to be detected. The term complementary as used herein means that the sequence of the probe is exactly hybridizing to the sequence of the target. Probes generally can be 5 to 50 nucleotides long and in more particular embodiments can be from 10 to 25 nucleotides or 15 to 20 nucleotides. Nucleotides include ribonucleotides, deoxyribonucleotides and modified nucleotides such as inosine or nucleotides containing modified groups which do not essentially alter their hybridization characteristics.

In one implementation, DNA molecule 602 may include a DNA sequence that is complementary to a table-ID sequence and function as a probe to identify target molecules (e.g., DNA molecule 600) that include the table-ID sequence. In a DNA digital data storage many hundreds or thousands of identical probes may be introduced to tag and identify DNA molecules having specific sequences such as table-ID sequences, field-ID sequences, and the like. A probe such as DNA sequence 602 may include a tag or label that allows for identification for further manipulation of the complementary DNA sequence 600. The probe DNA molecule 602 (or an oligonucleotide complementary to at least a portion of the target oligonucleotide) may include a reporter or a coupling agent for attachment of a reporter. The reporter or coupling agent can be attached to the polymeric backbone or any of the bases of the probe or complementary oligonucleotide. Techniques are known for attaching a reporter group to nucleotide bases (both natural and nonstandard bases). Examples of reporter groups include biotin, digoxigenin, spin-label groups, radio labels, DNA-cleaving moieties, chromaphores, and fluorophores such as fluoroscein. Examples of coupling agents include biotin or substituents containing reactive functional groups. The reporter group may then be attached to streptavidin or contain a reactive functional group that interacts with the coupling agent to bind the reporter group to the target or complementary oligonucleotide.

Figure 6B:
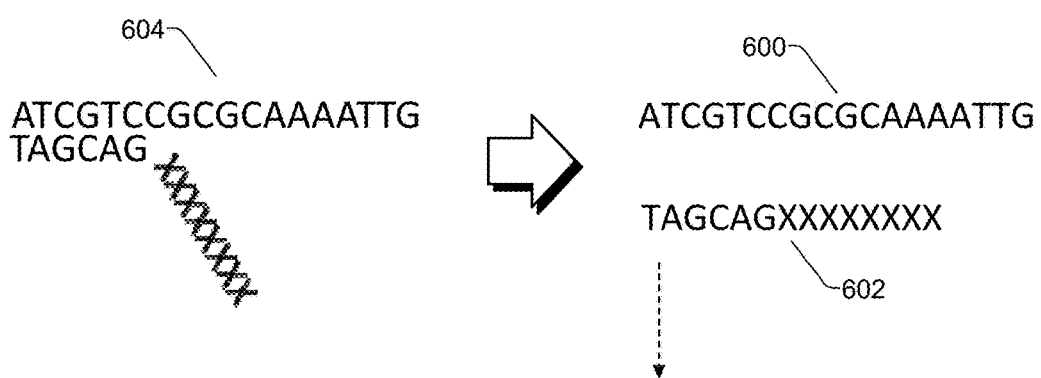

FIG. 6B shows a representation of DNA denaturation. DNA denaturation, also called DNA melting, is the process by which dsDNA unwinds and separates into ssDNA strands through the breaking of hydrophobic stacking attractions between the bases. Denaturation can be performed by heating, by altering salt concentration, or by inducing separation through the use of chemicals such as formaldehyde or urea. Appropriate techniques for denaturing the DNA under a given set of conditions are readily identifiable by those having ordinary skill in the art. Denaturation can separate the partially hybridized dsDNA molecule 604 back into the original ssDNA molecule 600 and ssDNA molecule 602. Denaturation may be used to remove a probe after analysis manipulations with the probe are completed. In one implementation, the ssDNA molecule 600 may be returned to a different chamber of the DNA digital data storage following denaturation.

Figure 7A:
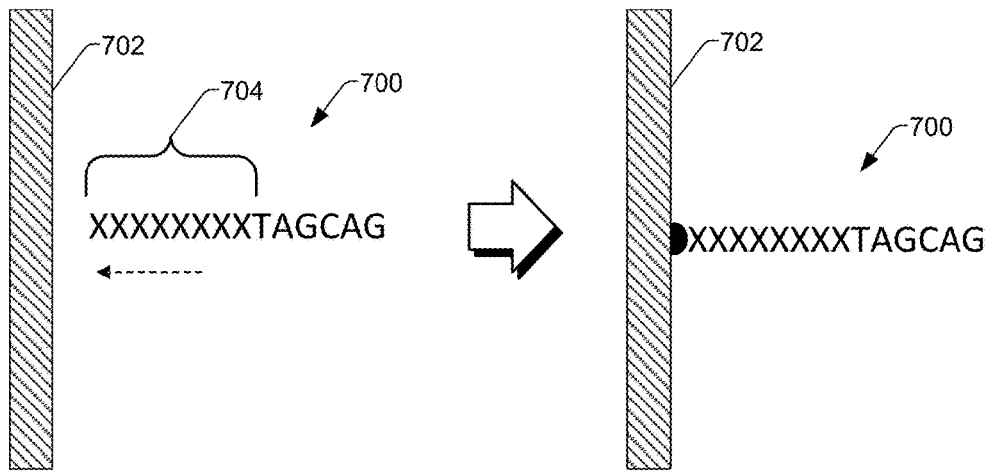
FIGS. 7A and 7B show attaching and separating a DNA molecule from a solid support.

FIG. 7A shows attachment of ssDNA molecule 700 to a solid support 702. The automated system 110 may be configured to attach DNA molecules to the solid support 702. The ssDNA molecule 700 may include a linker region 704 that separates the regions of interest in the ssDNA molecule 700 from the solid support 702. The linker region 704 may be a series of arbitrary or random DNA bases. Use of the linker region 704 may allow enzymes and other DNA molecules to interact with a distal end of the ssDNA molecule 700 without steric hindrance from the solid support 702. Many DNA manipulations may be carried out at least in part using a solid support. Generally, the captured DNA molecules are coupled to or otherwise disposed on a surface of the solid support. A variety of different supports can be used. In some implementations, the solid support is a single solid support, such as a chip or wafer, or the interior or exterior surface of a tube, cone, or other article. The solid support is fabricated from any suitable material to provide an optimal combination of such desired properties as stability, dimensions, shape, and surface smoothness. Preferred materials do not interfere with nucleic acid hybridization and are not subject to high amounts of non-specific binding of nucleic acids. Suitable materials include biological or non-biological, organic or inorganic materials. For example, the master array can be fabricated from any suitable plastic or polymer, silicon, glass, ceramic, or metal, and can be provided in the form of a solid, resin, gel, rigid film, or flexible membrane. Suitable polymers include, for example, polystyrene, poly(alkyl)methacrylate, poly(vinylbenzophenone), polycarbonate, polyethylene, polypropylene, polyamide, polyvinylidenefluoride, and the like.

Dimensions of the solid support are determined based upon such factors as the desired number of regions and the number of analyte-specific sequences to be assayed. As an example, a solid support can be provided with planar dimensions of about 0.5 cm to about 7.5 cm in length, and about 0.5 cm to about 7.5 cm in width. Solid supports can also be singly or multiply positioned on other supports, such as microscope slides (e.g., having dimensions of about 7.5 cm by about 2.5 cm) or even nano-scale supports or complex structures that are not planar. The dimensions of the solid support can be readily adapted for a particular application.

Other types of solid supports can be used. In some embodiments, the solid support is a particulate support. In these embodiments, the capture oligonucleotides are coupled to particles. Typically, the particles form groups in which particles within each group have a particular characteristic, such as, for example, color, fluorescence frequency, density, size, or shape, which can be used to distinguish or separate those particles from particles of other groups. In one implementation, the particles can be separated using techniques, such as, for example, flow cytometry.

Particulate supports can be fabricated from virtually any insoluble or solid material. For example, the particles can be fabricated from silica gel, glass, nylon, resins, Sephadex™, Sepharose™, cellulose, magnetic material, a metal (e.g., steel, gold, silver, aluminum, copper, or an alloy) or metal-coated material, a plastic material (e.g., polyethylene, polypropylene, polyamide, polyester, polyvinylidenefluoride (PVDF)) and the like, and combinations thereof Examples of suitable particles are available, for example, from Luminex Corp., Austin, Tex.

Typically, the support (whether a single or particulate support) is capable of binding or otherwise holding the capture oligonucleotide to the surface of the support in a sufficiently stable manner to accomplish the purposes described herein. Such binding can include, for example, the formation of covalent, ionic, coordinative, hydrogen, or van der Waals bonds between the support and the capture oligonucleotides or attraction to a positively or negatively charged support. Capture oligonucleotides are attached to the solid support surface directly or via linkers. In one embodiment, capture oligonucleotides are directly attached to the support surface by providing or derivatizing the surface, the oligonucleotide, or both, with one or more reactive groups. For example, the surface of the Luminex™ particles can be modified with, for example, carboxylate, maleimide, or hydrazide functionalities or avidin and glass surfaces can be treated with, for example, silane or aldehyde (to form Schiff base aldehyde-amine couplings with DNA). In some embodiments, the support or a material disposed on the support (as, for example, a coating on the support) includes reactive functional groups that can couple with a reactive functional group on the capture oligonucleotides. As examples, the support can be functionalized (e.g., a metal or polymer surface that is reactively functionalized) or contain functionalities (e.g., a polymer with pending functional groups) to provide sites for coupling the capture oligonucleotides.

As an alternative, the capture oligonucleotides can be retained on the surface by cross-linking of the capture oligonucleotides. Preferably, a capture oligonucleotide that is cross-linked includes a cross-linking portion and a capture portion, where the capture portion includes a molecular recognition sequence that hybridizes to the tagging sequence of the target oligonucleotide.

As yet another alternative, the support can be partially or completely coated with a binding agent, such as streptavidin, antibody, antigen, enzyme, enzyme cofactor or inhibitor, hormone, or hormone receptor. The binding agent is typically a biological or synthetic molecule that has high affinity for another molecule or macromolecule, through covalent or non-covalent bonding. The capture oligonucleotide is coupled to a complement of the binding agent (e.g., biotin, antigen, antibody, enzyme cofactor or inhibitor, enzyme, hormone receptor, or hormone). The capture oligonucleotide is then brought in contact with the binding agent to hold the capture oligonucleotide on the support. Other known coupling techniques can be readily adapted and used in the systems and methods described herein.

Figure 7B:
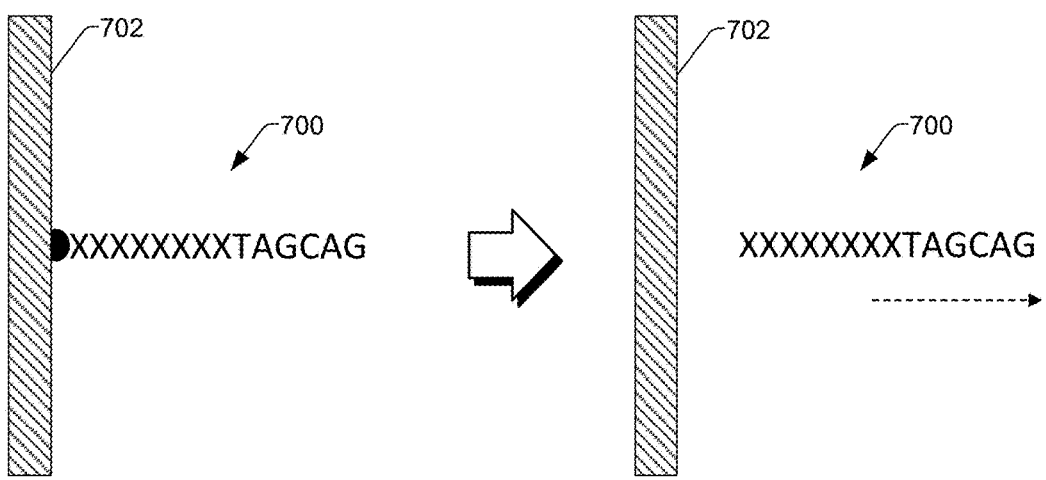

FIG. 7B shows separation of the ssDNA molecule 700 from the solid support 702. The ssDNA molecule 700 may be separated from the solid support 702 by breaking a covalent attachment that holds the ssDNA molecule 700 to the solid support 702. Additionally, separation may be achieved by cutting the linker region 704 of the ssDNA molecule 700. In implementations in which the ssDNA molecule 700 is held to the solid support 702 by annealing, the ssDNA molecule 700 may be displayed by another molecule that binds more strongly to the solid support 702. In one implementation, induced conformational change of a protein may release the ssDNA molecule 700 from the solid support 702. For example, the linker region 704 may be cut by use of a restriction enzyme.

Restriction enzymes (restriction endonucleases) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other.

An illustrative Type IIS restriction enzyme, whose cleavage domain is separable from the binding domain, is Fok I. This particular enzyme is active as a dimer. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a Fold cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are known to those of skill in the art.

Figure 8:
FIG. 8 shows washing a chamber containing DNA molecules with different sequences to remove DNA molecules that are not connected to a solid support.
Figure 8:
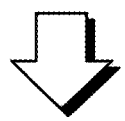
Figure 8:
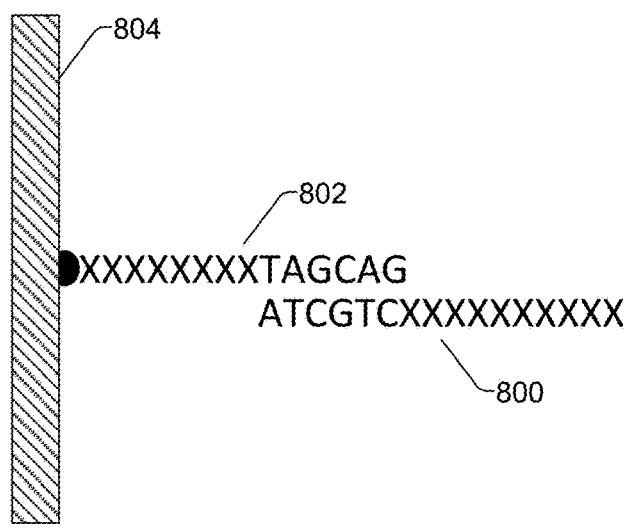

FIG. 8 shows selective hybridization of target DNA molecule 800 to a capture DNA molecule 802 which is attached to a solid support 804. Other DNA molecules 806 and 808 that do not include a region complementary to capture DNA molecule 802 do not hybridize to the capture DNA molecule 802 The capture DNA molecule 802 includes a molecular recognition sequence that can capture, by hybridization, the target DNA molecule 800 having a complementary tagging sequence. The hybridization of the molecular recognition sequence of the capture DNA molecule 802 and the tagging sequence of a target DNA molecule 800 results in the indirect coupling of the target DNA molecule 800 to the solid support 804. The molecular recognition sequence and tagging sequence may be associated with a particular analyte-specific sequence (also part of the target DNA molecule 800), thus indicating, if hybridization occurs, the presence or concentration of analyte with the analyte-specific sequence (or its complement) in the original sample.

The coding and tagging sequences typically include at least six nucleotides and, in some instances, include at least 8, 10, 15, or 20 or more nucleotides. In some assays, as described below, the molecular recognition sequence and tagging sequence include one or more non-standard bases.

In other assays, the molecular recognition sequence and tagging sequence do not contain non-standard bases.

The capture DNA molecule 802 may also include a functional group that permits binding of the capture DNA molecule 802 to the solid support 804 or functional groups disposed on or extending from the solid support 804. The functional group can be attached directly to the polymeric backbone or can be attached to a base in the nucleotidic sequence. As an alternative, the capture DNA molecule 802 can include a crosslinking portion to facilitate crosslinking, as described above, or can be electrostatically held on the surface. The capture DNA molecules 802 can be formed by a variety of techniques, including, for example, solid state synthesis, DNA replication, reverse transcription, restriction digest, run-off transcription, and the like.

In addition to the tagging sequence, the target DNA molecule 800 includes an analyte-specific sequence which corresponds to or is a complement to a sequence of interest in the analyte. The analyte-specific sequence can be independent from the tagging sequence or some or all of the tagging sequence can be part of the analyte-specific sequence.

The length of the capture DNA molecules 802 can be optimized for desired hybridization strength and kinetics. Usually, the length of the molecular recognition sequence is in the 6 to 20 (preferably, 8 to 12) nucleotide range. In a preferred embodiment, the different molecular recognition sequences of the capture DNA molecules 802 are not complementary to one another and, more preferably, to any known DNA fragment that has a significant probability of being present in a substantial amount in the DNA digital data storage. As a result, the capture molecular recognition sequences of the capture DNA molecule 802 will primarily hybridize to the respective complementary tagging sequences of the target DNA molecule 800.

Washing a chamber that contains the solid support 804 can remove the DNA molecules 806 and 808 while target DNA molecule 800 remains after the washing because it is hybridized to DNA molecule 802. This provides a technique for separation of DNA molecules based on hybridization. The washing conditions may be regulated to remove un-hybridized DNA molecules (e.g., DNA molecules 806 and 808) without removing DNA molecules that are hybridized (e.g., target DNA molecule 800) or otherwise directly or indirectly attached to the solid support 804. Depending on the washing conditions DNA molecules with relatively weak attachment (e.g., imperfect hybridization or hybridization over a short region) to the substrate may be removed during the washing. Thus, by varying the washing conditions the level of hybridization specificity needed for a DNA molecules remained in the chamber may be controlled. The washing may be performed with the solution that is used for storing the DNA in the DNA digital data storage. In one implementation the washing solution may be 10 mM Tris at a pH between 8 to 9.

One or more washes can be performed at the same or different levels of stringency. As another optional alternative, prior to contact with the support(s) and capture DNA molecule 802, the solution containing target oligonucleotides can be subjected to, for example, size exclusion chromatography, differential precipitation, spin columns, or filter columns to remove primers that have not been amplified or to remove other materials that are not the same size as the target oligonucleotides.

In some embodiments, multiple holders (e.g., vials, tubes, and the like) are used to assay multiple samples or have different combinations of capture DNA molecule 802 (and associated solid supports 804) within each holder. As another alternative, each holder can include a single type of capture DNA molecule 802 (and associated solid support 804).

As another example, the solid support 804 can be a group of individual support surfaces that are optionally coupled together. For example, the solid support 804 can include individual optical fibers or other support members that are individually coupled to different capture DNA molecules 802 and then bound together to form a single article, such as a matrix.

Detachment from the solid support 804 may be performed by denaturing the DNA strand 800 which is attached to the bound strand 802. This would leave the predicate or query portion of the DNA (e.g. capture DNA molecule 802), still bound to the substrate. Alternatively, the capture DNA molecule 802 could be physically separated from the substrate 804 and enter solution with the DNA strand of interest (not shown). Later denaturation could separate the capture DNA molecule 802 from the target DNA molecule 800 if necessary.

Figure 9:
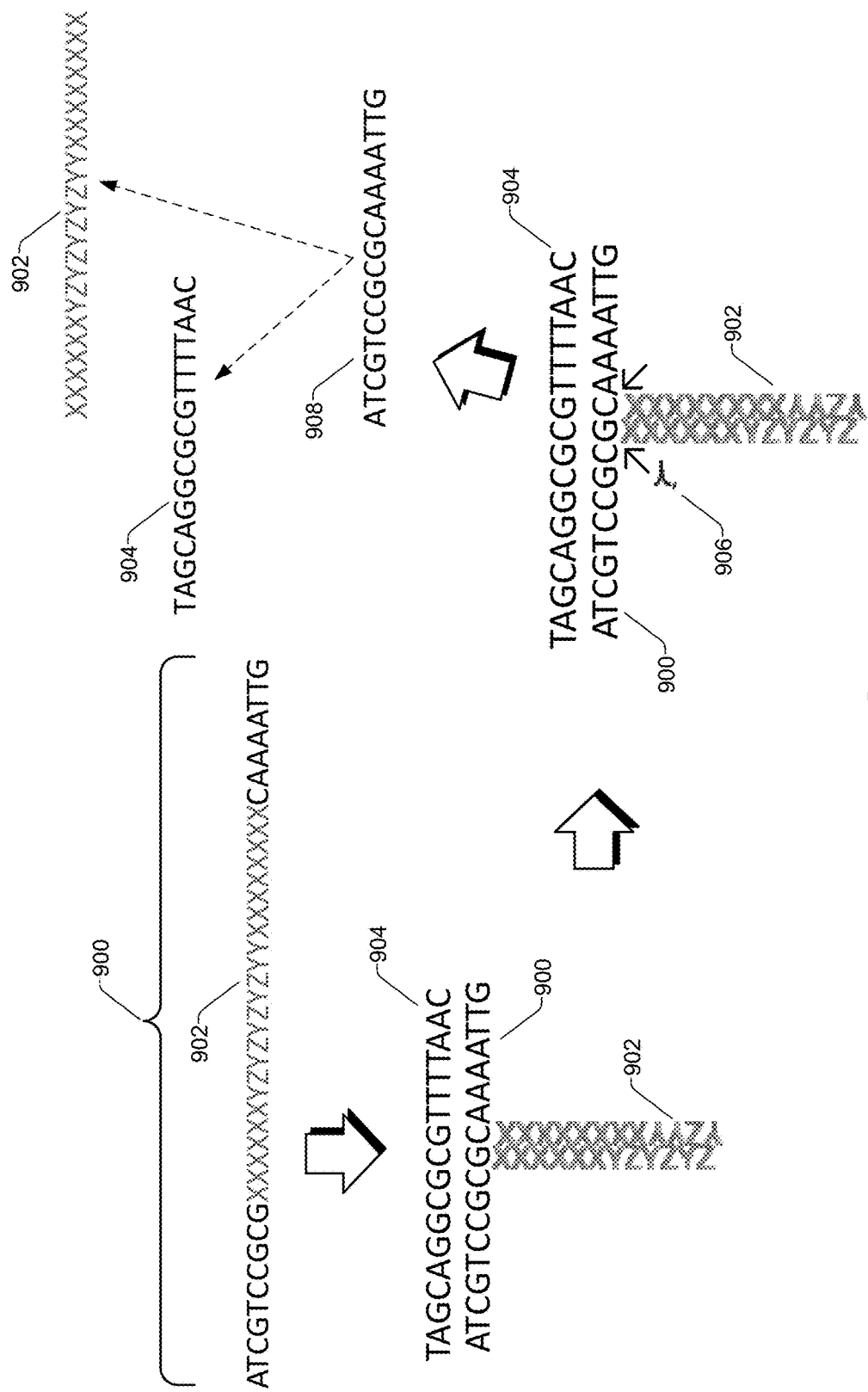
FIG. 9 shows a technique for removing a region of unknown DNA from a DNA molecule.

FIG. 9 shows a technique for removing a region of DNA flanked by two known sequences. A DNA molecule 900 may contain a region 902 of DNA that contains either a known or unknown sequence. This region 902 may be removed by hybridizing the DNA molecule 900 to a partially complementary DNA molecule 904 that is complementary to the sequences flanking the region 902 to be removed. The DNA region 902 to be removed forms a single-stranded loop and is removed. An enzyme 906 removes the DNA in the single-stranded loop. The loop formed by region 902 may be removed by Mung bean nuclease which selectively digests ssDNA. Mungbean Nuclease is a singlestrand-specific nuclease purified from sprouts of mung bean *Vigna radiata*. The enzyme degrades single-stranded DNA or RNA to nucleoside 5'-monophosphates, but does not digest double-stranded DNA, double-stranded RNA, or DNA/RNA hybrids. Mung Bean Nuclease catalyzes the specific degradation of single-stranded DNA or RNA, and produces mono and oligonucleotides carrying a 5'-P terminus. The loop formed by region 902 may also be removed by XPG endonuclease. The XPG endonuclease repairs DNA damage caused by ultraviolet light (UV light). The XPG endonuclease repairs DNA by a process called, Nucleotide excision repair. The XPG endonuclease has also been identified as functioning in the removal of hairpin loops.

After removal of the region 902, a nick remaining between the flanking sequences of the DNA molecule 900 may be repaired with DNA ligase. DNA ligase is a specific type of enzyme, a ligase, that facilitates the joining of DNA strands together by catalyzing the formation of a phosphodiester bond. DNA ligase plays a role in repairing single-strand breaks in duplex DNA. Denaturation separates the complementary DNA molecule 904 from the original DNA molecule 900 which is now reduced to a shorter DNA molecule 908 which omits the region 902. Although shown as a strand of DNA, the region 902 may be present as individual, separate nucleotides depending on the technique used to remove the single-stranded loop.

Figure 10:
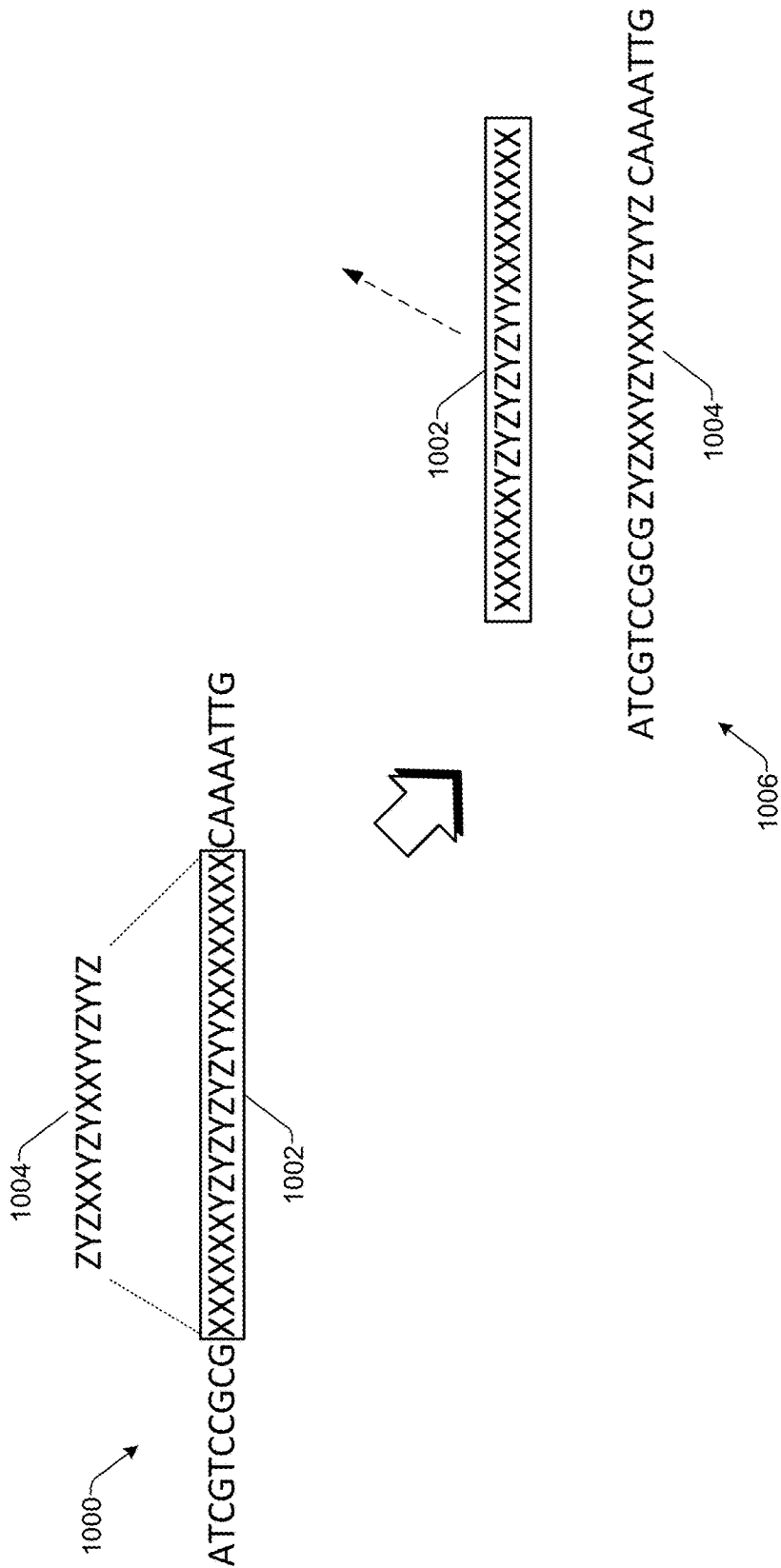
FIG. 10 shows a technique for replacing a region of known DNA with a different DNA sequence.

FIG. 10 shows a schematic representing replacement of a known sequence of DNA with an alternative sequence. DNA molecule 1000 includes region 1002 that is replaced by alternative sequence 1004. In one implementation, the replacement is performed by use of homologous recombination. The identified region of DNA 1002 can be excisable by any recombinase (e.g., Piggyback™, Cre-Loxp recombinase, and Flp recombinase). Vector designs of Piggyback™, Cre-Loxp recombinase, Flp recombinase for excision of nucleic acid sequences are known in the art. If desired, the vector may optionally contain flanking nucleic acid sequences that direct site-specific homologous recombination. The use of flanking DNA sequences to permit homologous recombination into a desired genetic locus is known in the art. At present it is preferred that up to several kilobases or more of flanking DNA corresponding to the insertion site be present in the vector on both sides of the encoding sequence (or any other sequence of this invention to be inserted into a location by homologous recombination) to assure precise replacement of sequences with the exogenous DNA.

Other site-specific genome-editing materials and methods besides homologous recombination are known in the art. In certain embodiments, a site-specific nuclease is introduced to the host cell that is capable of causing a double-strand break near or within a genomic target site. Site-specific nucleases useful with DNA digital data storages include, but are not limited to, transcription activator-like effector nucleases (TALENs), zinc-finger nucleases (ZFNs), and/or clustered regulatory interspaced short palindromic repeat (CRISPR)/Cas-based RNA-guided DNA endonucleases. TAL-effector nucleases are a class of nucleases that allow sequence-specific DNA cleavage, making it possible to perform site-specific DNA editing.

In one implementation, the DNA-binding domain is part of a CRISPR/Cas nuclease system. The CRISPR (clustered regularly interspaced short palindromic repeats) locus, which encodes RNA components of the system, and the cas (CRISPR-associated) locus, which encodes proteins make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Figure 11:
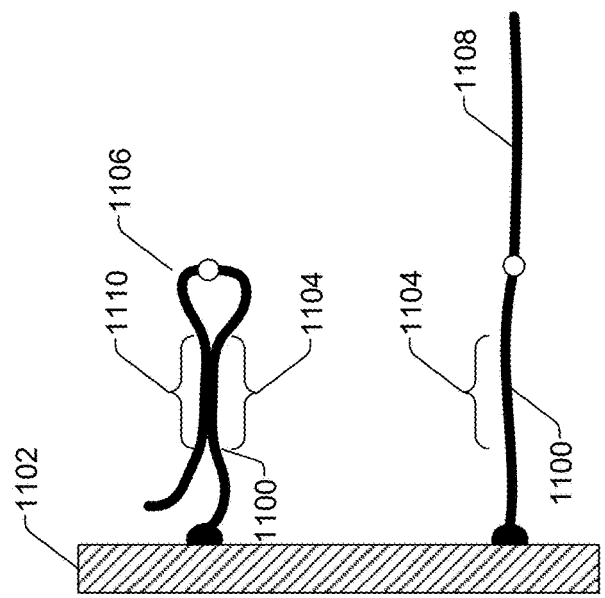
FIG. 11 shows a technique for identifying DNA molecules that include the same sequence by formation of hairpin loops.
Figure 11:
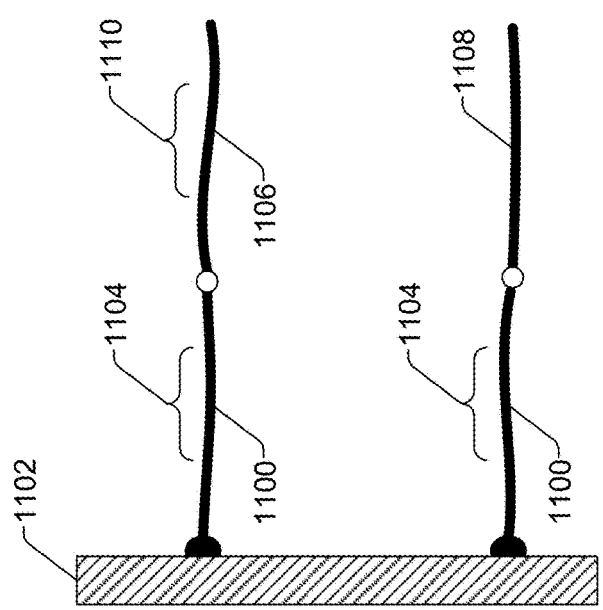

FIG. 11 shows a technique for using formation of hairpin loops to identify the presence of homologous regions in diverse DNA molecules. Multiple copies of DNA molecule 1100 are attached to a solid support 1102 by any of the techniques described herein as well as any other technique known in the art. This DNA molecule 1100 contains a region of interest 1104 that may be, for example, a field-ID sequence, a data region, or other sequence. The DNA molecules 1100 attached to the solid support 1102 are used to query other DNA molecules 1106 and 1108 to determine if there is a match with the region of interest 1104.

The other DNA molecules 1106 and 1108 which may be from a table or tables in the DNA digital data storage different from the DNA molecule 1100 are joined to a free end of one of the DNA molecules 1100 attached to the solid support 1102. The two DNA molecules may be joined end-to-end by DNA ligase in the presence of appropriate complementary DNA. For example, if the 3' end of DNA molecule 1100 is joined to the 5' end of DNA molecule 1106, the complementary DNA molecule may include a DNA sequence complementary to the 3'-end region of DNA molecule 1100 adjacent to a DNA sequence complementary to the 5'-end of DNA molecule 1106.

DNA molecule 1106 includes a region 1110 that is complementary to and hybridizes to the region of interest 1104. DNA molecule 1108 does not include any similar complementary sequences. A DNA base sequence that is identical will not hybridize, rather a complementary sequence hybridizes, thus when this technique is applied to analyzing a DNA digital data storage, DNA sequences 1106 and 1108 may be complementary sequences created from DNA molecules present in the DNA digital data storage. Hybridization between the sequence of interest 1104 and the sequence 1106 indicates that a DNA molecule complementary to DNA molecule 1106 (i.e., the original DNA molecule in the DNA digital data storage) contains the same sequence as the sequence of interest 1104.

The hybridization of complementary sequences between DNA molecules 1100 and 1106 may form a hairpin loop bound to the solid support 1102 but DNA molecules 1100 and 1108 that do not include complementary sequences do not form a hairpin loop. Selective isolation of DNA strands that form hairpin loops allows for identification of those DNA molecule pairs that contain homologous sequences (e.g., DNA molecules 1100 and 1106) from those that do not contain homologous sequences (e.g., DNA molecules 1100 and 1108).

Any suitable technique may be used to selectively isolate DNA strands that form hairpin loops. In one implementation, a microfluidics system with an opening large enough to allow ssDNA pass through but small enough to prevent transfer of DNA having a hairpin loop may be used to separate DNA molecules with hairpin loops from DNA molecules without hairpin loops. Differential speed of travel through an electrophoresis gel may also be used to separate DNA molecules with hairpin loops from those without. In one implementation, the hairpin loops may be formed in an environment that causes the hairpin loops to surround (i.e., loop around) another strand of DNA or other nano-structure. For example, this other strand of DNA (or other structure) can be positioned a distance from the surface of the solid support 1102 that is in the region where hairpin loops will be formed if complementary sequences of DNA are present. Upon separating DNA molecules 1100 and 1106 and 1100 and 1108 from the solid support 1102, ssDNA molecules will be free in solution while DNA molecules that have a hairpin loop will be anchored by the hairpin loop surrounding the other strand of DNA (or other structure) like a lasso. Washing to remove the DNA molecules in solution will separate those DNA molecules with hairpin loops from un-looped DNA molecules.

Illustrative DNA Manipulation-Relational Algebra Correlations

The relational algebra operation of selection may be implemented at least in part in a DNA digital data storage by attaching a table-ID-complement sequence complementary to a portion of the table-ID sequence targeted by the selection to one or more solid supports. The attachment to solid supports may be as shown and described in FIG. 7A. Hybridization conditions are created such that the table-ID-complement sequence holds complementary DNA sequences together during washing. Washing is performed on the chamber to remove DNA molecules that are free in solution as shown in FIG. 8. DNA molecules remaining in the chamber are isolated. Thus, this allows for identification of all DNA molecules that belong to a particular table.

Next, the DNA molecules may be separated from the solid support as shown in FIG. 7B. A field-ID-complement sequence complementary to a field-ID sequence target by the selection is attached to a solid support. Hybridization conditions are created such that the field-ID complement sequence holds DNA molecules having the field to the solid support by hybridization. Washing and isolation are performed as above yielding only those DNA molecules with the table-ID sequence that also have the field-ID sequence.

The relational algebra operation of selection may also be implemented at least in part in a DNA digital data storage by attaching a table-ID-complement sequence complementary to a portion of the table-ID sequence and a field-ID-complement sequence complementary to a field-ID sequence targeted by the selection to one or more solid supports. The attachment to solid supports may be as shown and described in FIG. 7A. The length of the table-ID-complement sequence and the washing conditions (e.g., pressure, temperature, and ionic concentration) may be selected so that the table-ID-complement sequence by itself does not hold complementary DNA sequences together during washing. Thus, an additional region of hybridization (i.e., the filed-ID complement sequence) becomes necessary to avoid removal of hybridized strands during washing.

Next, DNA from the DNA digital data storage is hybridized with the table-ID-complement sequence and the field-ID-complement sequence in a chamber such as chamber 114 shown in FIG. 1. Washing is performed on the chamber to remove DNA molecules that are free in solution as shown in FIG. 8. DNA molecules remaining in the chamber are isolated. Following isolation, the DNA molecules may be sequenced or may be subject to further manipulations.

Selections for different features can be applied iteratively by fixing all DNA through annealing that has the first desired characteristic, washing to remove the DNA in solution, releasing the DNA from the substrate, then again repeating the selecting and washing steps.

The selection operation may also be used to implement a range query by using metadata encoded in the DNA molecule (e.g., in a pre-defined separator 412 adjacent to a data region that includes the value which is targeted by the range query) that represents a magnitude or "bin" of values. For example, a database may contain one or more tables that include data regions encoding employee salaries. Each data region encoding a salary may be associated with a magnitude separately encoded in the DNA molecule. The magnitudes may be $0-$9999, $10,000-$19,999, $20,000-$29,999, $30,000-$39,999, $40,000-$49,999, $50,000-$59,999, $60,000-$69,999, $70,000-$79,999, $80,000-$89,999, $90,000-$99,999, and $100,000 or more. Each of these 11 magnitudes or "bins" of values may be represented by a different sequence of DNA bases. These magnitude sequences are pre-determined and known. Therefore, a range query for employee salaries between $30,000 and $60,000 may be implemented by first performing multiple selection operations that selects those DNA molecules which have magnitude sequences corresponding to $30,000-$39,999, $40,000-$49,999, $50,000-$59,999, and $60,000-$69,999 for employee salaries. Because there is not direct correspondence between the range specified in this range query and the values of the magnitudes encoded in the DNA, the DNA molecules isolated by this query will actually cover a salary range of $30,000-$69,999. In one implementation, these DNA molecules are sequenced and the range query is completed on the digital computer by removing the results for employee salaries from $60,001-$69,999. This is an example of jointly using DNA manipulations and digital computer calculations to return a result.

The relational algebra operation of projection may be implemented at least in part in a DNA digital data storage by synthesizing complementary DNA that is complementary to a first pre-defined separator and a second pre-defined separator. The pre-defined separators may be the separators 412 shown in FIG. 4. The first pre-defined separator is a DNA sequence between a first data region and a second data region in DNA from the DNA digital data storage and the second pre-defined separator is a DNA sequence between a third data region and a fourth data region in DNA from the DNA digital data storage.

Next, DNA from the DNA digital data storage is hybridized with the complementary DNA forming a ssDNA loop as shown in FIG. 9. The DNA loop formed between the first pre-defined field separator and the second pre-defined field separator is removed. This removal of DNA results in removal of fields from a table in the database that are not included in the projection. Following removal of the DNA loop the DNA is contacted with DNA ligase to repair the phosphate backbone. The remaining DNA is the results of the projection and includes portions of the DNA molecule that correspond to the fields present after the relational algebra operation of projection. Following removal of the DNA loop and ligation, the DNA from the DNA digital data storage is separated from the complementary DNA by denaturation as shown in FIG. 6B.

The relational algebra operation of intersection may be implemented at least in part in a DNA digital data storage by synthesizing DNA complementary to a pre-defined separator such as the pre-defined separator 412 shown in FIG. 4, attaching the DNA complementary to the pre-defined separator to a solid support as shown in FIG. 7A, and adding DNA of a table from the DNA digital data storage to a chamber such as chamber 114 of FIG. 1. The DNA complementary to the pre-defined separator, the DNA molecule attached to the solid support, is extended by synthesizing DNA complementary to a data region associated with the pre-defined separator thereby making a new segment of DNA that hybridizes to the data region.

Next the DNA complementary to the pre-defined separator and the DNA complementary to the data region from the DNA of the table is denatured leaving a DNA molecule attached to the solid support that includes a region complementary to the data region over which to perform the intersection operation. This is followed by washing the chamber to remove DNA in solution as shown in FIG. 8 and adding DNA from a second table from the DNA digital data storage to the chamber. The DNA from the second table hybridizes with the DNA complementary to the data region that is attached to the solid support if the DNA from the second table includes the same information in a data region. By washing the chamber again to remove free DNA molecules in solution, DNA molecules hybridized to the DNA complementary to the data region represent the intersection between the table and the second table and DNA molecules removed by the washing (which may be collected in a separate chamber) represent the set difference.

The relational algebra operation of rename may be implemented at least in part in a DNA digital data storage by contacting DNA from the DNA digital data storage with a site-specific nuclease system that is specific to a field-ID sequence, hybridizing the DNA following removal or replacement of the field-ID sequence with a DNA sequence complementary to a new field-ID sequence, and synthesizing or inserting the new field-ID sequence in the DNA. Removal of the field-ID sequence and addition of the new filed-ID sequence may be performed with techniques as shown and described in FIG. 10.

In one implementation, the rename operation may be effected on the DBMS of a DNA digital data storage by re-associating the specific DNA base sequence of the field-ID sequence with a new name. This does not change the DNA molecules, but rather alters the result returned by the DBMS for sequences that include the DNA base sequence of the field-ID.

The relational algebra operation of Cartesian product may be implemented at least in part in a DNA digital data storage by synthesizing template DNA complementary to (i) at least a portion of a 5'-end sequence of the DNA strand having the table-ID sequence and at least a portion of a 3'-end sequence of a DNA strand having a second known sequence such as a table-ID sequence or (ii) at least a portion of a 3'-end sequence of the DNA strand having the table-ID sequence and at least a portion of a 5'-end sequence of the DNA strand having the second known sequence. The template DNA is then hybridized with a DNA strand having the table-ID sequence and with a DNA strand having the second table-ID sequence.

Next the hybridized DNA is contacted with DNA ligase to create a single DNA molecule comprising the DNA strand having the table-ID sequence and the DNA strand having the second known sequence. Denaturing the template DNA from the single DNA molecule removes the template leaving a new DNA molecule that represents the Cartesian product of the table with the first table-ID and the table with the second known sequence.

This new table created through the Cartesian product operation may be given a new table-ID by hybridizing a strand of ssDNA that includes a region complementary to either the 3'-end sequence or the 5'-end sequence of the single DNA molecule and a region that includes a complementary sequence to the new table-ID. After hybridization, PCR using a known primer site in the DNA molecule encoding the new table is used to extend that DNA molecule along the sequence complementary to the new table-ID thereby appending the new table-ID onto the single DNA molecule encoding the new table. One of ordinary skill in the art will understand that this technique, including modifications of this technique, can be applied to add new table-IDs to tables created by operations other than Cartesian product.

The relational algebra operation of natural join may be implemented at least in part in a DNA digital data storage by providing DNA having a table-ID sequence to a chamber such as the chamber 114 shown in FIG. 1, synthesizing complementary DNA that is complementary to the provided DNA as shown in FIG. 5B, and attaching the complementary DNA to one or more solid supports as shown in FIG. 7A. In one implementation the complementary DNA may be synthesized prior to providing the DNA having the table-ID sequence to the chamber.

Next the DNA having the table ID is separated from the complementary DNA by denaturing as shown in FIG. 6B. That is followed by washing the chamber as shown in FIG. 8. The leaves the complementary DNA in the chamber and attached to the solid support. From this point the DNA manipulations described above for the operation of Cartesian product are performed. That will result in hairpin loops forming in some of the DNA molecules that are attached to the solid support as shown in FIG. 11.

Separating DNA having hairpin loops from DNA without hairpin loops identifies the strands of DNA in which the first table and the second table have the same data region values. In one implementation, DNA bound to the solid support and having hairpin loops may be separated from other DNA bound to the solid support by selectively separating the loop portions of the DNA from the remainder of the DNA molecule. Washing can remove the looped portions of DNA which are free in solution from the DNA molecules that did not form hairpin loops and still remain attached to the solid support. Restriction enzymes may be used to cut dsDNA at the "neck" of a hairpin loop to release the loop from the portion of the DNA molecule remaining attached to the solid support. Recall that the hairpin loops may be formed from data regions having the same values (and same nucleotide sequence) and that pre-defined separators may be adjacent to data regions. If the pre-defined separators (or other part of the DNA molecule) are designed to for restriction enzyme sites that are recognized by restriction enzymes only with present in dsDNA, then the pre-defined separators provide a point for cutting the DNA molecule to selectively remove the hairpin loops.

Multiple ones of the operations described above can be performed in series as a "pipeline". For example, the DNA molecules that result from an intersection operation may then be used as the starting point for performing a select operation. Complex operations that use multiple DNA-manipulation primitives may have multiple intermediate steps. All or some of the intermediate steps may create new tables and may also add a new table-ID sequence to the DNA molecules encoding the new tables. The new table ID may be used for table identification (e.g., through selective annealing) and further relational algebra operations producing a "pipeline".

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document. "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A system for performing relational algebra operations on a DNA digital data storage, the system comprising:
a first chamber containing a liquid suspension of a plurality of DNA molecules each encoding at least one row from a table of one or more tables in a relational database;
a controller configured to receive a series of instructions for manipulating the DNA molecules, wherein the instructions correspond to a relational algebra operation; and
an automated system configured to move a volume of liquid from the first chamber to a second chamber in response to the series of instructions from the controller.

Clause 2. The system of clause 1, wherein the automated system is further configured to attach some or all of the plurality of DNA molecules to a solid support.

Clause 3. The system of clause 1 or 2, further comprising an oligonucleotide synthesizer configured to synthesize DNA molecules that are complementary to a sequence of a table ID region, a field ID region, or data region of a one of the plurality of DNA molecules.

Clause 4. The system of any of clauses 1-3, further comprising a DNA sequencer configured to determine a sequence of all or part of one of the plurality of DNA molecules and provide the sequence to a digital computer.

Clause 5. The system of any of clauses 1-4, further comprising a digital computer configured to receive the relational algebra operation and translate the relational algebra operation into the series of instructions for manipulating the DNA molecules based at least in part on a sequence of a table ID region or a sequence of a field ID region of a one of the plurality of DNA molecules.

Clause 6. A system for performing relational algebra operations on a DNA digital data storage, the system comprising:
means for containing a liquid suspension of a plurality of DNA molecules each encoding at least one row from a table of one or more tables in a relational database;
means for receiving a series of instructions for manipulating the DNA molecules, wherein the instructions correspond to a relational algebra operation; and means for moving a volume of liquid from the first chamber to a second chamber in response to the series of instructions from the controller.

Clause 7. The system of clause 6, further comprising a means for attaching some or all of the plurality of DNA molecules to a solid support.

Clause 8. The system of clause 6 or 7, further comprising a means for synthesizing DNA molecules that are complementary to a sequence of a table ID region, a field ID region, or data region of a one of the plurality of DNA molecules.

Clause 9. The system of any of clauses 6-8, further comprising a means for determining a sequence of all or part of one of the plurality of DNA molecules and providing the sequence to a digital computer.

Clause 10. The system of any of clauses 6-9, further comprising a means for receiving the relational algebra operation and translating the relational algebra operation into the series of instructions for manipulating the DNA molecules based at least in part on a sequence of a table ID region or a sequence of a field ID region of a one of the plurality of DNA molecules.

Clause 11. A method comprising:
receiving a relational algebra operation specifying a table in a relational database, wherein the table is designated by a table-ID sequence;
identifying DNA manipulations corresponding to the relational algebra operation that include hybridizing a complementary DNA sequence to at least a portion of the table-ID sequence included in a DNA molecule;
sending instructions to perform the DNA manipulations to a DNA DBMS; and
receiving electronic data representing a DNA sequence from the DNA digital data storage.

Clause 12. The method of clause 11, wherein the relational algebra operation is selection and the method further comprises identifying the DNA manipulations to include:
attaching a table-ID-complement sequence that is complementary to a portion of the table-ID sequence and a field-ID-complement sequence that is complementary to a field-ID sequence targeted by the selection to one or more solid supports, wherein a length of the table-ID-complement sequence by itself does not hold complementary DNA sequences together during washing;
hybridizing DNA from the DNA digital data storage with the table-ID-complement sequence and at least one of the field-ID-complement sequence or a value of a data region in a chamber;
washing the chamber; and
isolating the DNA molecules remaining in the chamber.

Clause 13. The method of clause 11, wherein the relational algebra operation is projection and the method further comprises identifying the DNA manipulations to include:
synthesizing complementary DNA that is complementary to a first pre-defined separator and that is complementary to a second pre-defined separator, wherein the first pre-defined separator is a DNA sequence between a first data region and a second data region in DNA from the DNA digital data storage and the second pre-defined separator is a DNA sequence between a third data region and a fourth data region in DNA from the DNA digital data storage;
hybridizing the DNA from the DNA digital data storage with the complementary DNA;
removing a DNA loop formed between first pre-defined field separator and the second pre-defined field separator;
contacting the DNA following removal of the DNA loop with DNA ligase; and separating the DNA from the DNA digital data storage following removal of the DNA loop from the complementary DNA.

Clause 14. The method of clause 11, wherein the relational algebra operation is intersection and the method further comprises identifying the DNA manipulations to include:
wherein the table is a first table;
synthesizing DNA complementary to a pre-defined separator;
attaching the DNA complementary to the pre-defined separator to a solid support;
adding DNA of the first table to a chamber;
extending the DNA complementary to the pre-defined separator by synthesizing DNA complementary to a data region associated with the pre-defined separator;
denaturing the DNA complementary to the pre-defined separator and the DNA complementary to the data region from the DNA of the first table;
washing the chamber;
adding DNA from a second table from the DNA digital data storage to the chamber;
hybridizing the DNA from the second table with the DNA complementary to the data region that is attached to the solid support; and
washing the chamber, wherein DNA molecules hybridized to the DNA complementary to the data region represent the intersection and DNA molecules removed by washing represent the set difference.

Clause 15. The method of clause 11, wherein the relational algebra operation is rename and the method further comprises identifying the DNA manipulations to include:
contacting the DNA from the DNA digital data storage with a site-specific nuclease system that is specific to a field-ID sequence;
hybridizing the DNA following removal of the field-ID sequence with a DNA sequence complementary to a new field-ID sequence; and
synthesizing the new field-ID sequence in the DNA.

Clause 16. The method of clause 11, wherein the relational algebra operation is Cartesian product and the method further comprises identifying the DNA manipulations to include:
synthesizing template DNA complementary to (i) at least a portion of a 5'-end sequence of the DNA strand having the table-ID sequence and at least a portion of a 3'-end sequence of a DNA strand having a second table-ID sequence or (ii) at least a portion of a 3'-end sequence of the DNA strand having the table-ID sequence and at least a portion of a 5'-end sequence of the DNA strand having the second table-ID sequence;
hybridizing the template DNA with the DNA strand having the table-ID sequence and with the DNA strand having the second table-ID sequence;
contacting the hybridized DNA with DNA ligase to create a single DNA molecule comprising the DNA strand having the table-ID sequence and the DNA strand having the second table-ID sequence; and
denaturing the template DNA from the single DNA molecule.

Clause 17. The method of clause 11, wherein the relational algebra operation is natural join and the DNA manipulations comprise:
providing DNA having the table-ID sequence to a chamber;
synthesizing complementary DNA that is complementary to the provided DNA;

attaching the complementary DNA to one or more solid supports;

denaturing the DNA having the table ID from the complementary DNA;

washing the chamber;

performing the DNA manipulations of clause 16 using the second table-ID sequence; and separating DNA having hairpin loops from DNA without hairpin loops to identify strands of DNA from the first table and the second table that have the same data region values.

Clause 18. The method of one of clauses 11-17, further comprising identifying a set of DNA molecules in the DNA digital data storage that are the result of the relational algebra operation involving the DNA manipulations and wherein the DNA sequence from the DNA digital data storage includes only sequences of the set of DNA molecules.

Clause 19. The method of clauses 11-18, further comprising sending instructions to synthesize the complementary DNA sequence.

Clause 20. The method of clauses 11-18, further comprising determining that the complementary DNA sequence is pre-synthesized and available for use to query the DNA digital data storage.

Clause 21. A synthetic ssDNA molecule in a DNA digital data storage, the ssDNA molecule comprising:

a table-ID region identifying a table in the DNA digital data storage;

a field-ID region identifying a field of the table; and a data region representing data stored in the table.

Clause 22. The synthetic ssDNA molecule of clause 21, wherein the field-ID region is adjacent to the data region.

Clause 23. The synthetic ssDNA molecule of clause 21 or 22, further comprising a 5'-end sequence located on the 5' end of the ssDNA molecule and a 3'-end sequence located at the 3' end of the ssDNA molecule, wherein at least one of the 5'-end sequence or the 3'-end sequence contains a pre-defined primer site.

Clause 24. The synthetic ssDNA molecule of any of clauses 21-23, further comprising two data regions and a pre-defined separator between the two data regions.

Clause 25. The synthetic ssDNA molecule of any of clauses 21-24, further comprising two data regions and a separate instance of the table-ID region associated with each of the two data regions.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

---

The invention claimed is:

1. A method comprising:

receiving a relational algebra operation specifying a table in a relational database, wherein the table is designated by a table-ID sequence;

identifying DNA manipulations corresponding to the relational algebra operation that include hybridizing a complementary DNA sequence to at least a portion of the table-ID sequence included in a DNA molecule;

sending instructions to perform the DNA manipulations to a DNA DBMS; and receiving electronic data representing a DNA sequence from a DNA digital data storage, wherein the relational algebra operation is selection and the method further comprises identifying the DNA manipulations to include:

attaching a table-ID-complement sequence that is complementary to a portion of the table-ID sequence and a field-ID-complement sequence that is complementary to a field-ID sequence targeted by the selection to one or more solid supports, wherein a length of the table-ID-complement sequence by itself does not hold complementary DNA sequences together during washing;

hybridizing DNA from the DNA digital data storage with the table-ID-complement sequence and at least one of the field-ID-complement sequence or a value of a data region in a chamber;

washing the chamber; and isolating the DNA molecules remaining in the chamber.

2. The method of claim 1, further comprising sending instructions to synthesize the complementary DNA sequence.

3. The method of claim 1, further comprising determining that the complementary DNA sequence is pre-synthesized and available for use to query the DNA digital data storage.

4. The method of claim 1, further comprising identifying a set of DNA molecules in the DNA digital data storage that are the result of the relational algebra operation involving the DNA manipulations and wherein the DNA sequence from the DNA digital data storage includes only sequences of the set of DNA molecules.

5. A method comprising:

receiving a relational algebra operation specifying a table in a relational database, wherein the table is designated by a table-ID sequence;

identifying DNA manipulations corresponding to the relational algebra operation that include hybridizing a complementary DNA sequence to at least a portion of the table-ID sequence included in a DNA molecule;

sending instructions to perform the DNA manipulations to a DNA DBMS; and receiving electronic data representing a DNA sequence from a DNA digital data storage, wherein the relational algebra operation is projection and the method further comprises identifying the DNA manipulations to include:

synthesizing complementary DNA that is complementary to a first pre-defined separator and that is complementary to a second pre-defined separator, wherein the first pre-defined separator is a DNA sequence between a first data region and a second data region in DNA from the DNA digital data storage and the second pre-defined separator is a DNA sequence between a third data region and a fourth data region in DNA from the DNA digital data storage;

hybridizing the DNA from the DNA digital data storage with the complementary DNA;

removing a DNA loop formed between first pre-defined field separator and the second pre-defined field separator;

contacting the DNA following removal of the DNA loop with DNA ligase; and separating the DNA from the DNA digital data storage following removal of the DNA loop from the complementary DNA.

6. A method comprising:

receiving a relational algebra operation specifying a table in a relational database, wherein the table is designated by a table-ID sequence;

identifying DNA manipulations corresponding to the relational algebra operation that include hybridizing a complementary DNA sequence to at least a portion of the table-ID sequence included in a DNA molecule;

sending instructions to perform the DNA manipulations to a DNA DBMS; and receiving electronic data representing a DNA sequence from a DNA digital data storage, wherein the relational algebra operation is intersection and the method further comprises identifying the DNA manipulations to include:

wherein the table is a first table;

synthesizing DNA complementary to a pre-defined separator;

attaching the DNA complementary to the pre-defined separator to a solid support;

adding DNA of the first table to a chamber;

extending the DNA complementary to the pre-defined separator by synthesizing DNA complementary to a data region associated with the pre-defined separator;

denaturing the DNA complementary to the pre-defined separator and the DNA complementary to the data region from the DNA of the first table;

washing the chamber;

adding DNA from a second table from the DNA digital data storage to the chamber;

hybridizing the DNA from the second table with the DNA complementary to the data region that is attached to the solid support; and washing the chamber, wherein DNA molecules hybridized to the DNA complementary to the data region represent the intersection and DNA molecules removed by washing represent the set difference.

7. A method comprising:

receiving a relational algebra operation specifying a table in a relational database, wherein the table is designated by a table-ID sequence;

identifying DNA manipulations corresponding to the relational algebra operation that include hybridizing a complementary DNA sequence to at least a portion of the table-ID sequence included in a DNA molecule;

sending instructions to perform the DNA manipulations to a DNA DBMS; and receiving electronic data representing a DNA sequence from a DNA digital data storage, wherein the relational algebra operation is rename and the method further comprises identifying the DNA manipulations to include:

contacting the DNA from the DNA digital data storage with a site-specific nuclease system that is specific to a field-ID sequence;

hybridizing the DNA following removal of the field-ID sequence with a DNA sequence complementary to a new field-ID sequence; and synthesizing the new field-ID sequence in the DNA.

8. A method comprising:

receiving a relational algebra operation specifying a table in a relational database, wherein the table is designated by a table-ID sequence;

identifying DNA manipulations corresponding to the relational algebra operation that include hybridizing a complementary DNA sequence to at least a portion of the table-ID sequence included in a DNA molecule;

sending instructions to perform the DNA manipulations to a DNA DBMS; and receiving electronic data representing a DNA sequence from a DNA digital data storage, wherein the relational algebra operation is Cartesian product and the method further comprises identifying the DNA manipulations to include:

synthesizing template DNA complementary to (i) at least a portion of a 5'-end sequence of the DNA strand having the table-ID sequence and at least a portion of a 3'-end sequence of a DNA strand having a second table-ID sequence or (ii) at least a portion of a 3'-end sequence of the DNA strand having the table-ID sequence and at least a portion of a 5'-end sequence of the DNA strand having the second table-ID sequence;

hybridizing the template DNA with the DNA strand having the table-ID sequence and with the DNA strand having the second table-ID sequence;

contacting the hybridized DNA with DNA ligase to create a single DNA molecule comprising the DNA strand having the table-ID sequence and the DNA strand having the second table-ID sequence; and denaturing the template DNA from the single DNA molecule.

9. The method of claim 8, wherein the relational algebra operation is natural join and the DNA manipulations comprise:

providing DNA having the table-ID sequence to a chamber;

synthesizing complementary DNA that is complementary to the provided DNA;

attaching the complementary DNA to one or more solid supports;

denaturing the DNA having the table ID from the complementary DNA;

washing the chamber;

performing the DNA manipulations of claim 8 using the second table-ID sequence; and separating DNA having hairpin loops from DNA without hairpin loops to identify strands of DNA from the first table and the second table that have the same data region values.

10. A system comprising:

one or more processors; and a memory comprising a DNA digital data storage storing a synthetic ssDNA molecule, the ssDNA molecule comprising:

a table-ID region identifying a table in the DNA digital data storage;

a field-ID region identifying a field of the table; and a data region representing data stored in the table;

the memory further comprising instructions which, when executed by the one or more processors, cause the one or more processors to perform operations comprising:

receiving a relational algebra operation specifying the table in the DNA digital data storage identified by the table-ID region;

identifying DNA manipulations corresponding to the relational algebra operation that include hybridizing a complementary DNA sequence to at least a portion of the table-ID region included in the synthetic ssDNA molecule;

sending instructions to perform the DNA manipulations to the DNA digital data storage; and receiving electronic data representing a DNA sequence from the DNA digital data storage, wherein the relational algebra operation is selection and the memory further comprises instructions which, when executed by the one or more processors, cause the one or more processors to perform operations comprising identifying the DNA manipulations to include:

attaching a table-ID-complement sequence that is complementary to a portion of the table-ID region and a field-ID-complement sequence that is complementary to a field-ID sequence targeted by the selection to one or more solid supports, wherein a length of the table-ID-complement sequence by itself does not hold complementary DNA sequences together during washing;

hybridizing DNA from the DNA digital data storage with the table-ID-complement sequence and at least one of the field-ID-complement sequence or a value of a data region in a chamber;

washing the chamber; and isolating the DNA molecules remaining in the chamber.

11. The system of claim 10, wherein the field-ID region is adjacent to the data region.

12. The system of claim 10, the synthetic ssDNA molecule further comprising a 5'-end sequence located on the 5' end of the ssDNA molecule and a 3'-end sequence located at the 3' end of the ssDNA molecule, wherein at least one of the 5'-end sequence or the 3'-end sequence contains a pre-defined primer site.

13. The system of claim 10, the synthetic ssDNA molecule further comprising two data regions and a pre-defined separator between the two data regions.

14. The system of claim 10, the synthetic ssDNA molecule further comprising two data regions and a separate instance of the table-ID region associated with each of the two data regions.

* * * * *

SEQUENCE LISTING

```
<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: arbitrary sequence for illustrating structural
      properties

<400> SEQUENCE: 1
atcgtccgct a                                                           11

<210> SEQ ID NO 2
<211> LENGTH: 18
<212> TYPE: DNA
<213> ORGANISM: Artificial Sequence
<220> FEATURE:
<223> OTHER INFORMATION: arbitrary sequence for illustrating structural
      properties

<400> SEQUENCE: 2
atcgtccgcg caaaattg                                                    18

<210> SEQ ID NO 3
<211> LENGTH: 18
<212> TYPE: DNA
<213> ORGANISM: Artificial Sequence
<220> FEATURE:
<223> OTHER INFORMATION: arbitrary sequence for illustrating structural
      properties

<400> SEQUENCE: 3
tagcaggcgc gttttaac                                                    18

<210> SEQ ID NO 4
```

-continued

```
<211> LENGTH: 43
<212> TYPE: DNA
<213> ORGANISM: Artificial Sequence
<220> FEATURE:
<223> OTHER INFORMATION: arbitrary sequence for illustrating structural
      properties
<220> FEATURE:
<221> NAME/KEY: misc_feature
<222> LOCATION: (11)..(36)
<223> OTHER INFORMATION: n is a, c, g, or t

<400> SEQUENCE: 4
atcgtccgcg nnnnnnnnnn nnnnnnnnnn nnnnnncaaa atg                    43
```